US012626189B2

(12) United States Patent
Jessen et al.

(10) Patent No.: US 12,626,189 B2
(45) Date of Patent: May 12, 2026

(54) PREDICTING A DIAGNOSTIC TEST RESULT FROM PATIENT LABORATORY TESTING HISTORY

(71) Applicant: Laboratory Corporation of America Holdings, Burlington, NC (US)

(72) Inventors: Walter Joseph Jessen, New Palestine, IN (US); Stanley Ian Letovsky, Milton, MA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 749 days.

(21) Appl. No.: 18/055,279

(22) Filed: Nov. 14, 2022

(65) Prior Publication Data

US 2023/0145258 A1    May 11, 2023

Related U.S. Application Data

(60) Provisional application No. 63/298,925, filed on Jan. 12, 2022, provisional application No. 63/278,342, filed on Nov. 11, 2021.

(51) Int. Cl.
*G06F 7/00* (2006.01)
*G06F 17/00* (2019.01)
(Continued)

(52) U.S. Cl.
CPC ............. *G06N 20/00* (2019.01); *G16H 10/40* (2018.01); *G16H 15/00* (2018.01)

(58) Field of Classification Search
CPC ......... G06N 20/00; G16H 10/40; G16H 15/00
(Continued)

(56) References Cited

U.S. PATENT DOCUMENTS

| | | | | |
|---|---|---|---|---|
| 8,589,081 | B2 * | 11/2013 | Yundt-Pacheco | ...... G16H 10/40 |
| | | | | 702/19 |
| 9,326,008 | B2 * | 4/2016 | Kokaram | ............... H04N 19/65 |
| 2013/0266057 | A1 * | 10/2013 | Kokaram | ................. G06T 5/70 |
| | | | | 375/E7.227 |
| 2020/0005900 | A1 * | 1/2020 | Cha | ........................ G16H 10/40 |
| 2020/0270340 | A1 * | 8/2020 | Cook | ................... C07K 16/244 |

(Continued)

OTHER PUBLICATIONS

Castane et al., "Coupling Machine Learning and Lipidomics as a Tool to Investigate Metabolic Dysfunction—Associated Fatty Liver Disease. A General Overview", Biomolecules, vol. 11, No. 3, Mar. 22, 2021, 21 pages.

(Continued)

*Primary Examiner* — Pavan Mamillapalli
(74) *Attorney, Agent, or Firm* — Wolf, Greenfield & Sacks, P.C.

(57) ABSTRACT
The present disclosure relates to techniques for preprocessing samples and using preprocessed samples and machine learning models to predict clinical diagnostic tests for a patient from their historical laboratory testing data. Particularly, aspects are directed to obtaining datasets including features and/or historical laboratory test results for subjects, filtering the datasets based on a denoise-balance scheme to obtain filtered datasets, training a machine learning model using the filtered datasets to obtain a trained machine learning model, and providing the trained machine learning model. A candidate machine learning model may be an ensemble of classifiers implemented with a boosting algorithm, and the ensemble is trained by applying base machine learning algorithms on different distributions of the filtered datasets. The ensemble is then combined into a machine learning model having the set of learned model parameters for predicting results for clinical diagnostic tests.

17 Claims, 8 Drawing Sheets

(51) Int. Cl.

| | | |
|---|---|---|
| *G06N 20/00* | (2019.01) | |
| *G16H 10/40* | (2018.01) | |
| *G16H 15/00* | (2018.01) | |

(58) Field of Classification Search

USPC .......................................................... 706/12

See application file for complete search history.

(56) References Cited

U.S. PATENT DOCUMENTS

| | | | |
|---|---|---|---|
| 2020/0357526 A1* | 11/2020 | Odiz ....................... | G16H 20/10 |
| 2022/0122250 A1* | 4/2022 | Besson ................ | G06N 3/0464 |
| 2022/0300789 A1* | 9/2022 | DeLaRosa .............. | G06N 3/08 |
| 2022/0301113 A1* | 9/2022 | DeLaRosa ........... | G06N 3/0895 |
| 2022/0309618 A1* | 9/2022 | DeLaRosa ............. | G06N 3/048 |

OTHER PUBLICATIONS

Docherty et al., "Development of a Novel Machine Learning Model to Predict Presence of Nonalcoholic Steatohepatitis", Journal of the American Medical Informatics Association, vol. 28, No. 6, Mar. 4, 2021, pp. 1235-1241.

Feng et al., "Machine Learning Algorithm Outperforms Fibrosis Markers in Predicting Significant Fibrosis in Biopsy-Confirmed NAFLD", Journal of Hepato-Biliary-Pancreatic Sciences, vol. 28, No. 7, Jul. 2021, pp. 593-603.

Liu et al., "Comparison and Development of Advanced Machine Learning Tools to Predict Nonalcoholic Fatty Liver Disease: An Extended Study", Hepatobiliary and Pancreatic Diseases International, vol. 20, No. 5, Oct. 2021, pp. 409-415.

Ma et al., "Application of Machine Learning Techniques for Clinical Predictive Modeling: A Cross-Sectional Study on Nonalcoholic Fatty Liver Disease in China", Biomed Research International, vol. 2018, Oct. 3, 2018, 10 pages.

International Preliminary Report on Patentability issued in PCT/US2022/049866 dated May 23, 2024, 12 pages.

International Search Report and Written Opinion issued in PCT/US2022/049866 dated Feb. 15, 2023, 17 pages.

Wu et al., "Prediction of Fatty Liver Disease Using Machine Learning Algorithms", Computer Methods and Programs in Biomedicine, vol. 170, Mar. 2019, pp. 23-29.

* cited by examiner

200

300

400

500

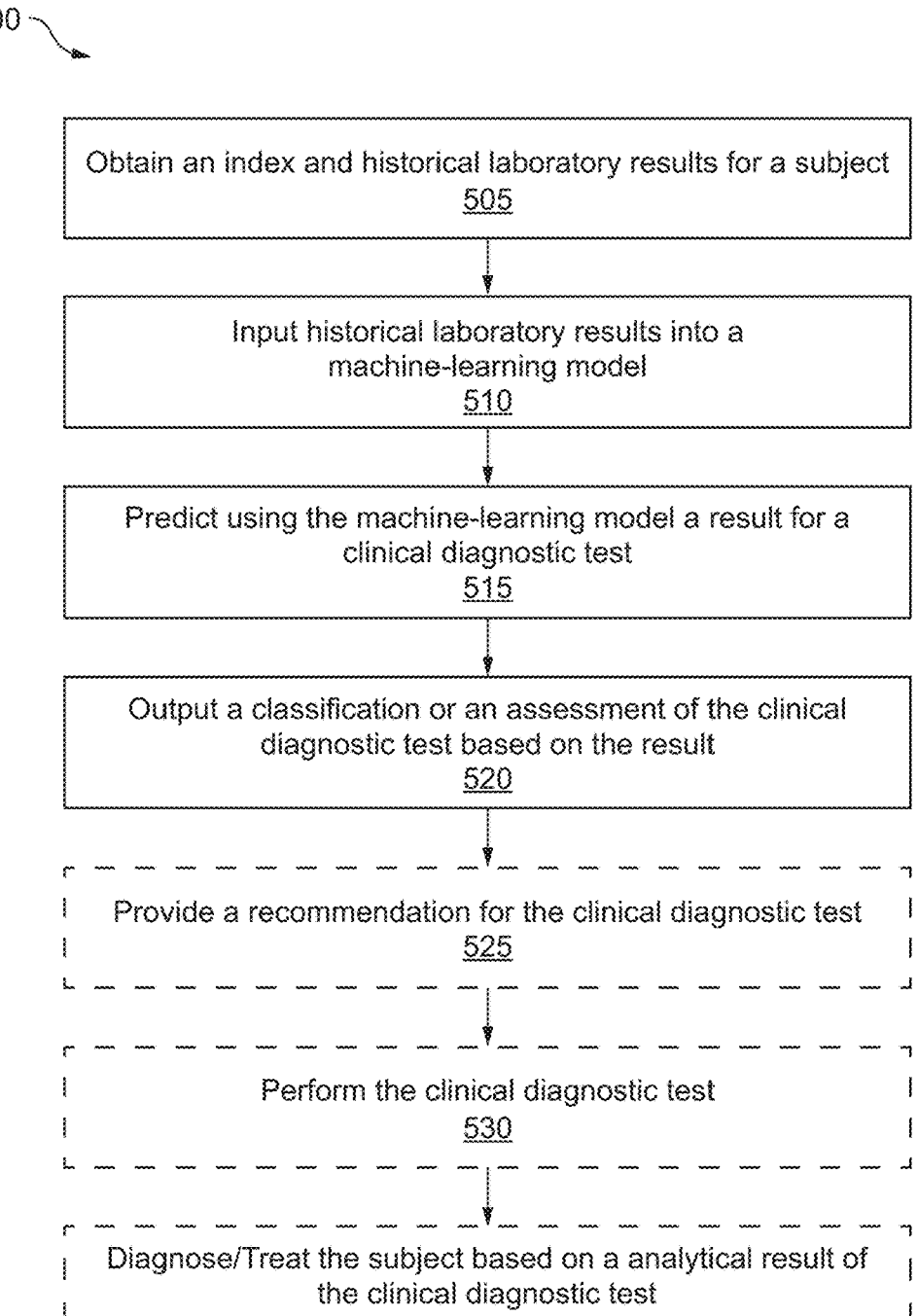

Obtain an index and historical laboratory results for a subject
505

Input historical laboratory results into a
machine-learning model
510

Predict using the machine-learning model a result for a
clinical diagnostic test
515

Output a classification or an assessment of the clinical
diagnostic test based on the result
520

Provide a recommendation for the clinical diagnostic test
525

Perform the clinical diagnostic test
530

Diagnose/Treat the subject based on a analytical result of
the clinical diagnostic test
535

FIG. 5

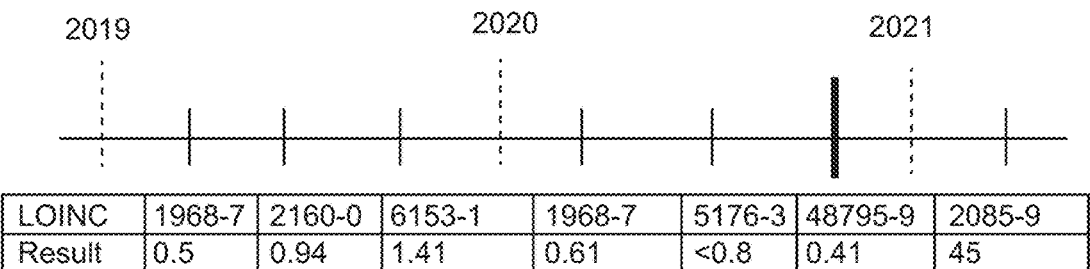
| LOINC | 1968-7 | 2160-0 | 6153-1 | 1968-7 | 5176-3 | 48795-9 | 2085-9 |
|-------|--------|--------|--------|--------|--------|---------|--------|
| Result | 0.5 | 0.94 | 1.41 | 0.61 | <0.8 | 0.41 | 45 |
| Label | 1968-7 | 2160-0 | 2085-9 | | 4548-4 |
|-------|--------|--------|--------|---|--------|
| 1 | 0.61 | 0.94 | -1 | ... | -1 |
FIG. 6

PREDICTING A DIAGNOSTIC TEST RESULT FROM PATIENT LABORATORY TESTING HISTORY

CROSS REFERENCE TO RELATED APPLICATIONS

The present application claims priority and benefit from U.S. Provisional Application No. 63/298,925, filed Jan. 12, 2022, and U.S. Provisional Application No. 63/278,342, filed Nov. 11, 2021, the entire contents of which are incorporated herein by reference for all purposes.

FIELD

The present disclosure relates to clinical testing, and in particular to techniques for preparing samples and using machine learning models to predict clinical diagnostic test results for a patient from their historical laboratory test results.

BACKGROUND

Clinical laboratories are healthcare facilities providing a wide range of laboratory procedures which aid clinicians in carrying out the diagnosis, treatment, and management of patients. Clinical laboratories report most laboratory test results as individual numerical or categorical values. However, individual test results, viewed in isolation, are typically of limited diagnostic value. To adequately use test results for patient diagnosis and management, clinicians usually must integrate many individual test results from a patient and interpret them in the context of clinical data and medical knowledge, judgment, and experience. While this manual approach to test result interpretation is the current standard in most cases, computational approaches to laboratory data integration and analysis offer tremendous potential to enhance diagnostic value. In particular, many patients will have hundreds or thousands of these individual test results, often spanning years. As a consequence, many clinicians can easily overlook key results or important patterns and trends within sets of laboratory data. Furthermore, important diagnostic information may sometimes be contained within patterns across numerous data elements that may be too subtle or complex to identify without the aid of computational approaches. In addition, because the human brain faces great challenges in simultaneously considering a large number of data points, even the most experienced clinicians may be unable to extract all the useful information from existing clinical and laboratory data.

SUMMARY

In various embodiments, a computer-implemented method is provided that comprises: obtaining datasets for subjects, wherein each of the datasets comprises subject features, wherein the subject features comprise an index and historical laboratory test results corresponding to test codes; filtering the datasets based on a denoise-balance scheme to obtain filtered datasets, wherein the denoise-balance scheme comprises an index filter, a test code filter, a feature filter, and a balance filter, and wherein the filtered datasets comprise filtered features; training a machine learning model using the filtered datasets to obtain a trained machine learning model; and providing the trained machine learning model.

In some embodiments, the filtering the datasets comprises: denoising the subject features based on the index filter, wherein the denoising comprises removing a first set of the datasets from the datasets; denoising the subject features based on the test code filter, wherein the denoising comprises removing a second set of the datasets from the datasets; obtaining at least two subsets of the datasets based on a historical laboratory test result corresponding to a predetermined test code, wherein the historical laboratory test is in the subject features; calculating a feature number for each subject feature in each subset based on the feature filter; sorting a total feature number, wherein the total feature number is a sum of at least two of the feature numbers for the at least two subsets; denoising the subject features based on the feature filter, wherein the denoising comprises removing a third set of the datasets from the datasets; and balancing the feature numbers based on the balance filter, wherein a ratio of the at least two feature numbers is in a predetermined range, wherein the balancing comprises removing a fourth set of the datasets from the datasets.

In some embodiments, the obtaining the at least two subsets of the datasets comprises removing datasets from at least one of the at least two subsets.

In some embodiments, the calculating the feature number comprises removing datasets from the at least two subsets to maintain a predetermined ratio scope between the at least two sub sets.

In some embodiments, the predetermined test code is a Non-Alcoholic Steatohepatitis (NASH) fibrosis score test code.

In some embodiments, the predetermined test code is albumin/creatinine ratio (ACR).

In some embodiments, the predetermined test code is estimated glomerular filtration rate (eGFR).

In some embodiments, the predetermined ratio scope is about [1:5, 5:1].

In some embodiments, the feature filter determines a number of the filtered features for the machine learning model.

In some embodiments, the number of the filtered features is equal to or less than 150.

In some embodiments, the training the machine learning model comprises: obtaining a first subset of the filtered datasets as training data, wherein the first subset of the filtered datasets comprises: (i) a set of outcome predictor datasets including historical laboratory test results for subjects that tested abnormal for a clinical diagnostic test, and (ii) a set of control datasets including historical laboratory test results for subjects that tested normal for the clinical diagnostic test; training a supervised machine learning model on the training data; validating the supervised machine learning model using a second subset of the filtered datasets as validation data; adjusting the supervised machine learning model by repeating the obtaining, the training, and the validating until a predetermined condition is satisfied; in response to the adjusting, obtaining a set of model parameters; and providing the trained machine learning model having the set of the model parameters.

In some embodiments, the supervised machine learning model adopts an ensemble method.

In some embodiments, the training the supervised machine learning model further comprises: training an ensemble of classifiers implemented with a boosting algorithm on the training data by applying base machine learning algorithms on different distributions of the training data, wherein the training causes the ensemble of classifiers to learn a function that maps a training input space derived from the sets of training data to a target output space such that the function is an accurate predictor for the target output space, wherein the target output space is a result of the clinical diagnostic test, and wherein the function is learned by finding the set of model parameters that minimize a cost function that measures a difference between ground truth values for the subjects that tested abnormal or normal for the clinical diagnostic test and predicted results of the clinical diagnostic test; in response to the training, obtaining the set of the model parameters; and combining the ensemble of classifiers into the trained machine learning model having the set of the model parameters for predicting the result for the clinical diagnostic test.

In some embodiments, the boosting algorithm is an adaptive boosting algorithm.

In some embodiments, the validating the supervised machine learning model comprises testing the ensemble of classifiers by applying the base machine learning algorithms with the set of the model parameters on different distributions of the validation data.

In some embodiments, abnormal for the clinical diagnostic test is based on a threshold value greater than or equal to a decision threshold defined by (i) selected sensitivity, (ii) selected recall, (iii) precision, (iv) positive predictive value, or (v) a combination thereof for the machine learning model.

In some embodiments, normal for the clinical diagnostic test is based on a threshold value less than a decision threshold defined by (i) selected sensitivity, (ii) selected recall, (iii) precision, (iv) positive predictive value, or (v) a combination thereof for the machine learning model.

In some embodiments, a date on which the abnormal or normal clinical diagnostic test occurred is determinative of which of the historical laboratory test results are used as the training data.

In some embodiments, all of the historical laboratory test results occurring prior to the date on which the abnormal or normal clinical diagnostic test occurred are used as the training data.

In some embodiments, the computer-implemented method further comprising: obtaining a dataset for a subject, wherein the dataset comprises an index and historical laboratory test results corresponding to test codes; inputting the dataset into the trained machine learning model; predicting, using the trained machine learning model, a result for a clinical diagnostic test; and outputting, using the trained machine learning model, a classification of the clinical diagnostic test based on the result for the clinical diagnostic test.

In some embodiments, the machine learning model is deployed on an invocable end point within a cloud infrastructure.

In some embodiments, the computer-implemented method further comprising invoking, using the invocable end point, the machine learning model via an application programming interface.

In some embodiments, the classification of the clinical diagnostic test comprises comparing the result for the clinical diagnostic test to a predefined threshold and classifying the clinical diagnostic test as abnormal or normal based on the comparison.

In some embodiments, the computer-implemented method further comprising providing a recommendation for the clinical diagnostic test based on the classification of the clinical diagnostic test.

In some embodiments, the computer-implemented method further comprising performing the clinical diagnostic test on a sample from the subject to obtain an analytical result for the clinical diagnostic test.

In some embodiments, the computer-implemented method further comprising diagnosing and/or treating the subject based on the analytical result for the clinical diagnostic test.

In some embodiments, a system is provided that includes one or more data processors and a non-transitory computer readable medium containing instructions which, when executed on the one or more data processors, cause the one or more data processors to perform part or all of one or more methods or processes disclosed herein.

In some embodiments, a computer-program product is provided that is tangibly embodied in a non-transitory machine-readable medium and that includes instructions configured to cause one or more data processors to perform part or all of one or more methods disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present invention will be better understood in view of the following non-limiting figures, in which:

FIG. 5 shows a flowchart illustrating a process for using a machine learning model to predict a clinical diagnostic test result in accordance with various embodiments.

FIG. 6 shows an example of how test data is preprocessed in accordance with various embodiments.

Figure 1:
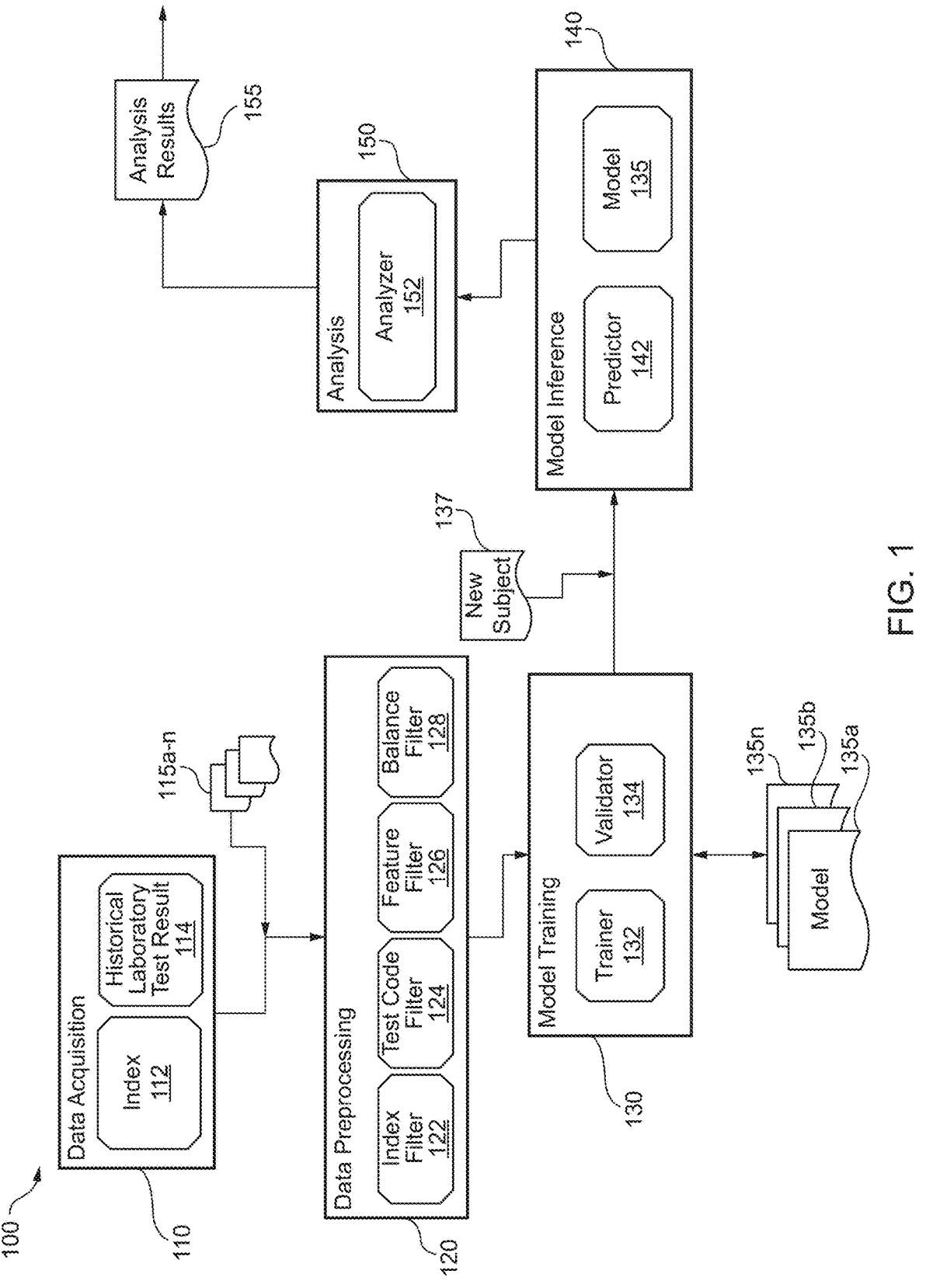
FIG. 1 shows a block diagram illustrating a system for implementing techniques for preprocessing datasets for subjects, using the pre-processed datasets to train a machine learning model, and using the trained model to predict a clinical diagnostic test result for a subject from their historical laboratory test results in accordance with various embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

I. Introduction

Machine learning (ML) has had tremendous impacts on numerous areas of modern society. For example, it is used for filtering spam messages from text documents, such as e-mail, analyzing various images to distinguish differences, and extraction of important data from large datasets through data mining. ML makes it possible to uncover patterns, construct models, and make predictions by learning from training data. ML algorithms are used in a broad range of domains, including biology and genomics. Deep learning (DL) is a subset of ML that differs from other ML processes in many ways. Most ML models perform well due to their custom-designed representation and input features. Using the input data generated through that process, ML learns algorithms, optimizes the weights of each feature, and optimizes the final prediction. DL attempts to learn multiple levels of representation using a hierarchy of multiple layers. In recent years, DL has overtaken ML in many areas, including speech, vision, and natural language processing. DL and ML are also increasingly used in the medical field, mainly in the areas of image analysis, drug research and development, data mining from medical documents, and speech. In addition to image and text data from medical charts generated in hospitals, various types of laboratory data may also be analyzed, which are mostly composed of numbers assigned various units of measurement. However, very few DL and/or ML models have been developed to analyze laboratory data. Moreover, the performance of ML/DL models is heavily dependent on the quality of training data, and researchers devote much more effort to preparing high-quality training data, whereas they still face the challenge that it is extremely harder to prepare high-quality training data in the field of laboratory analysis and clinical testing.

In practice, the symptoms described by patients, physical examinations performed by physicians, laboratory test results, and imaging studies such as X-ray and computed tomography (CT) are generally needed to evaluate a patient's status and diagnose a specific disease. Electronic clinical decision support represents an important tool to improve evaluation of these various clinical datasets and the efficiency with which diagnostic data can be converted into useful information. The main purpose of clinical decision support is to provide timely information to clinicians, patients, and others to inform decisions about health care. Examples of clinical decision support tools include order sets created for particular conditions or types of patients, recommendations, and databases that can provide information relevant to particular patients, reminders for preventive care, and alerts about potentially dangerous situations. Rule-based algorithms provide the foundation for most conventional clinical decision support tools. Rule-based algorithms tend to be easier to develop, validate, implement, and explain and can often be adapted directly from guidelines or literature. However, rule-based algorithms applied in clinical practice provide decision support based only on previously established knowledge.

To address these limitations, challenges, and problems, statistically algorithm-based approaches are disclosed herein that offer an opportunity to combine knowledge discovery with knowledge application to provide more accurate decision support based on previously unknown patterns. These previously unknown patterns are discovered and implemented to make inferences with respect to clinical decision support (e.g., recommendation of a diagnostic laboratory test to inform a clinician of a possible disease state for a patient) using machine learning models.

In an illustrative embodiment, a method is provided that comprises: obtaining datasets for subjects, wherein each of the datasets comprises subject features, wherein the subject features comprise an index and historical laboratory test results corresponding to test codes; filtering the datasets based on a denoise-balance scheme, wherein the denoise-balance scheme comprises an index filter, a test code filter, a feature filter, and a balance filter; in response to the filtering, obtaining filtered datasets, wherein each of the filtered datasets comprise filtered features; training a machine learning model using the filtered datasets to obtain a trained machine learning model; and providing the trained machine learning model.

In another illustrative embodiment, a method is provided that comprises: obtaining datasets for subjects, wherein each of the datasets comprises subject features, wherein the subject features comprise an index and historical laboratory test results corresponding to test codes; filtering the datasets based on a denoise-balance scheme, wherein the denoise-balance scheme comprises an index filter, a test code filter, a feature filter, and a balance filter, wherein the filtering comprises denoising the subject features based on the index filter, wherein the denoising comprises removing a first set of the datasets from the datasets; denoising the subject features based on the test code filter, wherein the denoising comprises removing a second set of the datasets from the datasets; obtaining at least two subsets of the datasets based on a historical laboratory test result corresponding to a predetermined test code, wherein the historical laboratory test result is in the subject features; calculating a test-code number for each subset based on the feature filter; sorting a total test-code number, wherein the total test-code number is a sum of at least two of the test-code numbers for the at least two subsets; removing a third set of the datasets from the datasets based on the feature filter; and balancing the test-code numbers based on the balance filter, wherein a ratio of the two test-code numbers is in a predetermined range, wherein the balancing comprises removing a fourth set of the datasets from the datasets; in response to the filtering, obtaining filtered datasets, wherein each of the filtered datasets comprise filtered features; training a machine learning model using the filtered datasets to obtain a trained machine learning model; and providing the trained machine learning model.

As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. As used herein, when an action is "based on" something, this means the action is based at least in part on at least a part of the something.

As used herein, the term "result" or "laboratory test result" means a value determined as a result of performing a single laboratory test or a score determine as a result of performing one or more laboratory tests. In some instances, the value is numerical such as 1.0, 2.5, 19.7, 25.0, etc. In other instances, the value is alpha such as negative, abnormal, positive, normal, etc. In other instances, the value is alpha numeric such as abnormal between 2.0 and 5.0 or the like.

As used herein, the term "abnormal" is defined as a state, condition, or behavior that is unusual or different from what is considered normal. For example, "abnormal" in certain instances means a result value for a clinical diagnostic test (i) greater than or equal to a decision threshold defined by a selected sensitivity/recall/precision/positive predictive value for a machine learning model, (ii) less than a decision threshold defined by a selected sensitivity/recall/precision/positive predictive value for a machine learning model, (iii) falling outside of a decision threshold interval defined by a selected sensitivity/recall/precision/positive predictive value for a machine learning model, or (iv) not identical to a predetermined condition. As used herein, the term "normal" is defined as a state, condition, or behavior that is typical, usual, or natural. For example, "normal" in certain instances means a result value for a clinical diagnostic test (i) less than or equal to a decision threshold defined by a selected sensitivity/recall/precision/positive predictive value for a machine learning model, (ii) greater than a decision threshold defined by a selected sensitivity/recall/precision/positive predictive value for a machine learning model, (iii) falling into a decision threshold interval defined by a selected sensitivity/recall/precision/positive predictive value for a machine learning model, or (iv) identical to a predetermined condition."

As used herein, the terms "a set of," "a subset of," and "an nth set of" (e.g., "a first set of," "a second set of") are defined as being largely but not necessarily wholly what is specified (and include wholly what is specified) as understood by one of ordinary skill in the art. In any disclosed embodiment, the term "a set of," "a subset of," or "an nth set of" may be substituted with "a part of" or "a section of" what is specified, where the part or section includes an empty part and a whole part.

II. Laboratory Test Result Predication Models and Techniques

In various embodiments, machine learning models and techniques are provided that predict the result of the one or more clinical diagnostic tests based on patient laboratory testing history to accurately identify patients trending towards an abnormal diagnostic test result and to support clinicians and healthcare organizations by potentially informing diagnosis early. Conventional approaches for predicting laboratory results and diagnostics use human intuition, or at the best, statistical-based approaches using limited or preselected laboratory tests. Human intuition is typically unreliable and cannot be expanded to large quantitative analysis, which may result in escalating costs for both patients and the industry. The conventional statistical-based approaches typically target specific tests and involves hypotheses specific to the targeted tests. Moreover, the preselected tests either bring noise or are not sufficient in obtaining support features to provide accurate predictions to the target tests.

In order to overcome these challenges and others, techniques described herein provide universally adaptable approaches to predict results for clinical diagnostic tests based on various features. In machine learning and pattern recognition, a feature is an individual measurable property or characteristic of a phenomenon being observed such as historical laboratory test results. The techniques denoise and balance the features before training machine learning models, which result in a substantial improvement in providing accurate predictions. These techniques are suitable for a variety of clinical diagnostic tests associated with diagnosis of a variety of health conditions. For example, the techniques may be used to predict results for a Nonalcoholic fatty liver disease (NAFLD) activity score (NAS), which is a composite score of steatosis, lobular inflammation, cytological ballooning, and fibrosis (disease stage) for diagnosing Non-Alcoholic Steatohepatitis (NASH), Albumin/Creatinine Ratio (ACR), also known as urine microalbumin, which helps identify kidney disease that can occur as a complication of diabetes, and estimated glomerular filtration rate (eGFR), which is a calculation that is used to determine how well the kidneys are filtering waste and help diagnose various stages of kidney disease such as Chronic Kidney Disease (CKD). Nonetheless, as should be understood, the use of the techniques is not limited to predicting results for these three clinical diagnostic tests and associated health conditions. Instead, the techniques have a wide range of applicability for predicting results of a variety of clinical diagnostic tests associated with diagnosis of a variety of health conditions.

As mentioned above, these techniques denoise and balance the features before training machine learning models. The denoising and balancing are performed in accordance with a denoise-balance scheme to filter and preprocess patient samples (e.g., datasets comprising the features) and use the preprocessed samples to train machine learning algorithms to provide more accurate predictions of results for clinical diagnostic tests, comparing with conventional human-intuitive or statistical-based approaches. The denoise-balance scheme is configured to reduce dimensionality of the training datasets while keeping as much variation as possible, which essentially projects the data to a lower dimensional subspace in order capture the fundamental nature of the data. The number of input variables or features for a dataset is referred to as its dimensionality. However, the performance of machine learning algorithms can degrade with too many input variables. For example, machine learning problems that involve many features make training extremely slow and tend to cause the machine learning algorithms overfit on the training data. Most data points in high-dimensional space are very close to the border of that space. This is because there is plenty of space in high dimensions. In a high-dimensional dataset, most data points are likely to be far away from each other. Therefore, the machine learning algorithms cannot effectively and efficiently train on the high-dimensional data.

Therefore, in some instances it is often desirable to reduce the number of input features. Dimensionality reduction refers to techniques that reduce the number of input variables in a dataset. High-dimensionality statistics and dimensionality reduction techniques are often used for data visualization. Nevertheless, these techniques can be applied in machine learning to simplify a dataset in order to better fit a predictive model. There are mainly two types of dimensionality reduction methods for machine learning. One type of technique only keeps the most important features in the dataset and removes the redundant features. There is no transformation applied to the set of features. Backward elimination, Forward selection and Random forests are examples of this method. The other technique uses linear or nonlinear methods to find a combination of new features. An appropriate transformation is applied to the set of features. The new set of features contains different values instead of the original values. Nonetheless, all of these techniques can be computationally intensive (i.e., require a lot of processing and memory resources) and lead to some amount of data loss (e.g., loss in data variation), which can possibly affect the performance of trained machine learning models.

In order to overcome these challenges and others, the techniques described herein filter patient samples based on a denoise-balance scheme that comprises different types of filters, for example, index filters, test code filters, feature filters, and balance filters. Different types of the filters may function differently to provide filtered samples, and the functions of filters may overlap in some degree. For example, index filters and test code filters may both provide the function of filtering samples based on a test code or a test date. Filtered or preprocessed samples are obtained and provided to machine learning algorithms for training and validating machine learning models. Advantageously, the various filtering and balancing techniques described herein (e.g., index filters, test code filters, feature filters, balance filters, or any combination thereof) are capable of being implemented using less processing and memory resources than conventional dimensionality reduction techniques and minimize the data loss that can be prevalent in some conventional dimensionality reduction techniques.

FIG. 1 is a block diagram illustrating a system 100 for implementing techniques for preprocessing datasets for subjects, using the preprocessed datasets to train a model, and using the trained model to predict a clinical diagnostic test result for a subject from their historical laboratory test results in accordance with various embodiments. In various instances, the techniques and functionalities described in this disclosure may be implemented by a system (optionally within a distributed environment) using a set of integrated devices that input, output, process, and store data and information. As shown in FIG. 1, the system 100 in this example includes several subsystems: a data acquisition subsystem 110, a data preprocessing subsystem 120, a model training subsystem 130, a model inference subsystem 140, and an analysis subsystem 150.

The data acquisition subsystem 110 is configured to obtain and store datasets for subjects. The datasets comprise indexes 112 and test results 114. The indexes 112 may include identifiers, age, gender, test date, test codes (e.g., LOINC codes, NDC codes, SNOMED-CT codes, and the like), and similar information regarding subjects 115. The test results 114 may include historical test results or scores (e.g., a fibrosis score, a glomerular filtration rate, a platelet count, a white blood cell count, an IgE allergy score, an iron saturation score, a creatinine, a potassium, a therapeutic drug level, and the like) for subjects 115. In some instances, the datasets are acquired from a clinical laboratory or health care system (e.g., analytical chemistry system, hematology system, patient record system, clinical trial testing system, and the like). In some instances, the datasets are acquired from a data storage structure such as a database, a laboratory or hospital information system, or the like associated with the one or more modalities for acquiring historical laboratory test results for subjects. The data acquisition subsystem 110 is further configured to provide the datasets to the data preprocessing subsystem 120.

The data preprocessing subsystem 120 includes an index filter 122, a test code filter 124, a feature filter 126, and a balance filter 128. The data preprocessing subsystem 120 is configured to filter the datasets based on a denoise-balance scheme to obtain filtered datasets. In the data preprocessing subsystem 120, the index filter 122 denoises the datasets for the subjects (e.g., subject features) based on index information and remove a first set of the datasets from the datasets. In some instances, datasets for subjects with unknown gender are removed by the index filter 122. In some instances, datasets for subjects falling outside of a predetermined age range (e.g., an age range is [18, 90]) are removed by the index filter 122. In some instances, a value of a historical laboratory test result for an earlier test date is reset to a default value by the index filter 122 if a test code of the historical laboratory test result for the earlier test date is the same test code for a later test date. In some instances, a value of a historical laboratory test result is reset to a default value by the index filter 122 if a test date for the historical laboratory test result is missing or in an incorrect format or falls outside of a predetermined score range. In some instances, a value of a historical laboratory test result is reset to a default value by the index filter 122 if a test date for the historical laboratory test result is prior to a predetermined date. It should be understood that any combination of the hereinbefore and hereinafter instances can be performed in any order or in parallel.

In the data preprocessing subsystem 120, the test code filter 124 denoises the datasets for the subjects based on test code information and remove a second set of the datasets from the datasets. In some instances, datasets for subjects with a historical laboratory test result for a predetermined test code (e.g., a "skip test") are removed by the test code filter 124. In some instances, datasets for subjects without a historical laboratory test result for a predetermined test code (e.g., a "required test") are removed by the test code filter 124. In some instances, a value of a historical laboratory test result for a predetermined test code for a subject is reset to a default value by the test code filter 124 if the value of a historical laboratory test result for the subject is missing or in an incorrect format or falls outside of a predetermined score range. In some instances, datasets for subjects with a value of a historical laboratory test result are removed by the test code filter 124 if a test date for the historical laboratory test result is later than a predetermined date or a date determined by the data preprocessing subsystem 120.

In the data preprocessing subsystem 120, the feature filter 126 obtains at least two subsets of the datasets based on a historical laboratory test result corresponding to a predetermined test code, calculates a feature number for each subject feature in each subset, sorts a total feature number, denoises the subject features and removes a third set of the datasets from the datasets. In some instances, the feature filter 126 performs splitting the datasets for the subjects into subsets based on the feature information, counting a number for one or more features in each subset, sorting a combined number, removing features based on a predetermined schedule, and removing unqualified datasets. In some instances, the datasets for the subjects are split based on a predetermined test code by the feature filter 126. In some instances, the predetermined test code is a test code for NASH fibrosis score. In some instances, the predetermined test code is a test code for albumin/creatinine ratio (ACR). In some instances, the predetermined test code is a test code for estimated glomerular filtration rate (eGFR). In some instances, datasets for subjects that are in at least two subsets are removed from the at least two subsets by the feature filter 126. In some instances, the predetermined test code used by the feature filter 126 is the same test code as that used in the test code filter 124. In some instances, datasets for a group of subjects are removed from a subset by the feature filter 126 if a predetermined ratio scope between the at least two subsets is not met. In some instances, a feature number is calculated for each feature in a subset by counting a number of subjects with the feature in the subset by the feature filter 126. In some instances, a total feature number is calculated for each feature by counting a sum of the number of the subjects with the feature in two or more subsets by the feature filter 126. In some instances, total feature numbers for all features are sorted by the feature filter 126. In some instances, certain features are removed from each dataset of the subjects by the feature filter 126. In some instances, the certain features are removed based on a predetermined schedule by the feature filter 126. In some instances, a certain number of sorted features are preserved, and the rest are removed from each dataset of the subjects by the feature filter 126. The certain number is equal to or less than 150. In some instances, the certain number is about 10, 20, 30, 40, 50, 60, 70, 80, 90, 100, 110, 120, 130, 140, or 150. In some instances, datasets for a group of subjects are removed by the feature filter 126 if a number of preserved features of the subject is less than a predetermined level comparing to a total number of preserved features of the subsets. In some instances, datasets for a group of subjects are removed by the feature filter 126 if a number of preserved features of the subject is less than a predetermined number. In some instances, the predetermined number is about 10, 20, 30, 40, 50, 60, 70, 80, 90, 100, 110, 120, 130, 140, or 150.

In the data preprocessing subsystem 120, the balance filter 128 balances the feature numbers. In some instances, the balance filter 128 balances the feature numbers based on a predetermined range. In some instances, a number of datasets in each subset that are determined by the feature filter 126 is determined by the balance filter 128. In some instances, a ratio of the number of datasets between each subset is determined by the balance filter 128. In some instances, the ratio of the number of datasets between each subset is compared to the predetermined range and datasets for a group of the subjects are removed from a subset by the balance filter 128 to meet the predetermined range. In some instances, the predetermined range is about 1. In some instances, the removal of the datasets for the group of the subjects are performed by the balance filter 128 in a random manner. In some instances, the removal of the datasets for the group of the subjects are performed by the balance filter 128 based on the frequency of the preserved features. In some instances, the datasets for the group of the subjects that have the least number of preserved features are first removed by the balance filter 128. In some instances, the balance filter 128 also performs a de-identification function and a combination of subsets function. In some instances, at least one index or feature of the datasets for the subjects is replaced by a default value by the balance filter 128. In some instances, an index or a feature of a dataset for a subject with a predetermined value is removed from the dataset by the balance filter 128. In some instances, at least two of the subsets are combined to a set of filtered datasets with filtered features by the balance filter 128. In some instances, a value in a filtered feature of a filtered dataset for a subject is the same value as a value in the same feature of a dataset for the subject. In some instances, a value in a filtered feature of a filtered dataset for a subject is a different value than a value in the same feature of a dataset for the subject. In some instances, the balance filter 128 provides the filtered datasets with the filtered features to the model training subsystem 130.

The model training subsystem 130 includes a trainer 132 and a validator 134. In the model training subsystem 130, models 135 are trained using datasets provided by a prior subsystem. In some instances, the datasets used to train the models 135 are the filtered datasets with the filtered features provided by the data preprocessing subsystem 120. In some instances, the model training subsystem 130 relabels the datasets provided by the prior subsystem as (i) a set of outcome predictor datasets including historical laboratory test results for subjects that tested abnormal for one or more clinical diagnostic test, and (ii) a set of control datasets including historical laboratory test results for subjects that tested normal for the one or more clinical diagnostic tests. In some instances, the normal or abnormal clinical diagnostic test result is predetermined by a prior subsystem based on selected sensitivity/recall/precision/positive predictive value. In some instances, the normal or abnormal clinical diagnostic test result is determined by the model training subsystem 130 based on selected sensitivity/recall/precision/positive predictive value. In some instances, the normal or abnormal clinical diagnostic test result is predetermined through human interaction. For example, a disease/diagnostic expert may be consulted to identify one or more clinical diagnostic tests to be used for achieving a given task or endpoint. The one or more clinical diagnostic tests may then be used to identify outcome predictor data for subjects that tested abnormal for the one or more clinical diagnostic tests and identify control data for subjects that tested normal for the one or more clinical diagnostic tests. Table 1 provides examples of various diseases of interest and test results identified by a disease/diagnostic expert that could be used for achieving a given task or endpoint for the various diseases of interest. Table 2 provides examples of various tasks or endpoints that a model may be configured to perform such as predicting whether a subject test score or result for the one or more clinical diagnostic tests will fall into an abnormal category.

TABLE 1

| Index | Disease | Test result used |
|---|---|---|
| 1 | Chronic kidney disease (CKD) | Glomerular filtration rate (eGFR) and/or albumin/creatinine ratio (ACR) |
| 2 | Non-alcoholic steatohepatitis (NASH) | Fibrosis score |
| 3 | Hemochromatosis | Iron saturation |
| 4 | Thrombocytopenia | Platelet count |
| 5 | Neutropenia | Neutrophil count |
| 6 | Hyperparathyroidism | Parathyrin intact (iPTH) levels |
| 7 | Allergy IgE | Other Allergy IgE |
| 8 | Diabetic Kidney Disease | eGFR, albumin/creatinine ratio, and/or and Hemoglobin (Hb) A1c |
| 9 | Kidney Disease | ACR (albumin/creatinine ratio) |

TABLE 2

| Endpoint | Description |
|---|---|
| Binary abnormal | Predicts whether a patients test result will fall into an 'abnormal' category as defined by the published reference range. For example, an A1C > 6.1 is "abnormal", while under may be considered "normal'. The model would provide an output of a probability (0.62 for example) that a given test is abnormal. |
| Low-normal-high | The model can be calibrated to explicitly look at tests that have a low and high reference range. There would thus be two probabilities, a probability that a given ordered test would be low and one that would be high. |
| Numerical (regression) | The model can be tuned to give a continuous numerical output, which can give a prediction of the actual test result. Additionally, confidence intervals can be provided for a given prediction. |
| Conditional | As in the chronic kidney disease model, the model requires two tests to be 'abnormal' to identify the condition. |
| Inclusion criteria driven | In the face of a clinical trial, additional inclusion/exclusion criteria can be imposed as criteria. For example, in chronic kidney disease, a specific clinical trial may want to only look at diabetics with chronic kidney disease, so the model may only target an endpoint that includes a diabetes ICD-10 code (or A1C test value) and look specifically at eGFR or ACR. |
| Temporal progression | An endpoint may look specifically for progression of a disease, for example CKD stage 2 to CKD stage 3, or pre-diabetes to diabetes. |
| Recommendation | Analogous to the "online shopping" model, where statements like "patients like me also tested abnormal for X, Y, Z" could be generated. This would allow for the identification of a universe of abnormal outcomes. For example, allergy IgE testing has over 400 tests, but often only 12 or less tests can be ordered in a single order (per insurance guidelines). A recommendation-based approach can help identify which of the 400 tests are best for the patient. This can also be used for rare disease, therapeutic drug monitoring, blood disorders, etc. |

The model training subsystem 130 builds and trains models 135a-135n ('n' represents any natural number) (which may be referred to herein individually as a model 135 or collectively as the models 135) to be used by the other subsystems for a given task or endpoint. The model 135 can be a machine learning model, such as (i) a convolutional neural network ("CNN"), e.g. an inception neural network, a residual neural network ("Resnet"), a U-Net, a V-Net, a single shot multibox detector ("SSD") network, or a recurrent neural network ("RNN"), e.g., long short-term memory ("LSTM") models or gated recurrent units ("GRUs") models, or any combination thereof, (ii) a linear model, (iii) a regression model, (iv) a support vector machine, (v) a naïve Bayes model, or (vi) a decision tree model. The model can also be any other suitable machine learning model trained for a given task or endpoint, such as a three-dimensional CNN ("3DCNN"), a dynamic time warping ("DTW") technique, a hidden Markov model ("HMI"), etc., or combinations of one or more of such techniques—e.g., CNN-HMM or MCNN (Multi-Scale Convolutional Neural Network). The system 100 may employ the same type of model or different types of models for a given task or endpoint.

The models and techniques described herein may use various machine learning algorithms and methods, such as an ensemble-based approach, to prediction. For example, the model 135 can be an ensemble of base models (e.g., decision trees or neural networks) combined via bagging, boosting, or stacking to create an optimal predictive model, e.g., a boosting model such as an AdaBoost or Gradient Boosting model. The following descriptions provide an illustrative example of using ensembled methods to train models. It is to be clearly understood that the descriptions are made only by way of example and not as limitation on the scope of the disclosure. Ensembles combine multiple hypotheses to form a more suitable hypothesis that makes accurate predictions. Ensemble learning combines several base algorithms to form one optimized predictive algorithm. For example, a typical decision tree for classification takes several factors, turns them into rule questions, and given each factor, either makes a decision or considers another factor. The result of the decision tree can become ambiguous if there are multiple decision rules, e.g., if threshold to make a decision is unclear or new sub-factors are input for consideration. This is where ensemble methods can help to form a more suitable hypothesis. Instead of being reliant on one decision tree to make the right call or be accurate, ensemble methods take several different trees and aggregate them into one final more suitable hypothesis that operates as a strong predictor.

In various embodiments, the models implement a boosting technique as the ensemble method. The boosting algorithm tries to build a strong learner (predictive model) from the mistakes of several weaker models. Boosting makes 'n' number of models during the model training period. Initially, boosting starts by creating a first model (e.g., a decision tree) from the training data. As the first model is made and errors from the first model are noted by the boosting algorithm, the sample or record which is incorrectly classified is used as input for a subsequent model. The subsequent model is generated from the previous model (e.g., the first model) by trying to reduce the errors from the previous model. Models are added sequentially, each correcting its predecessor, until the training data is predicted perfectly, or a maximum number of models have been added to the ensemble. Essentially, the boosting tries to reduce the bias error which arises when models are not able to identify relevant trends in the data. This happens by evaluating a difference between the predicted value of the model and the actual value or ground truth value assigned the training data. There are various types of boosting that may be implemented such as adaptive boosting (AdaBoost), gradient tree boosting, or XGBoost.

In certain instances, the models implement an adaptive boosting technique as the ensemble method. AdaBoost combines multiple weak classifiers to build one strong classifier. A weak classifier is one that performs better than random guessing, but still performs poorly at designating classes to objects. A single weak classifier may not be able to accurately predict the class of an object, but when multiple weak classifiers are grouped with each one progressively learning from the others' wrongly classified objects, a single strong model can be generated. The classifier could be any classifier such as a decision trees, logistic regression, or the like. Generating the single strong model may be implemented via a training process comprising generating a weak classifier (e.g., a decision tree) using training data based on weighted samples (e.g., laboratory test results). The weights of each sample indicate how important it is to be correctly classified. Initially, for the first model, all the samples may have equal weights. A weak classifier for each variable (e.g., laboratory tests) may be generated and a determination may be made as to how well each weak classifier classifies samples to their target classes. For example, a first subset of laboratory test results may be evaluated, and a determination is made as to how many samples are correctly or incorrectly classified as abnormal or normal for a given diagnostic test for each weak classifier. More weight is assigned to the incorrectly classified samples so that they're classified correctly in the next weak classifier in the ensemble. Weight may also be assigned to each classifier based on the accuracy of the classifier, which means high accuracy is equal to high weight. Thereafter the training process is reiterated until all the samples have been correctly classified, or a maximum iteration level has been reached.

To train a model 135 by the model training subsystem 130, the trainer 132 is comprised of three main subsystems or services: dataset preparation, feature engineering, and model training. The dataset preparation facilitates the process of loading datasets, splitting the datasets into training and validation datasets so that the system can train and test models 135, and performing basic machine learning preprocessing (e.g., standardization, normalization, tokenizing data, annotation, augmentation, etc.). In some instances, the datasets are acquired from a data storage structure such as a database, a computing system (e.g., data preprocessing subsystem 120), or the like. The splitting may be performed randomly (e.g., a 90/10% or 70/30%) or the splitting may be performed in accordance with a more complex validation technique such as K-Fold Cross-Validation, Leave-one-out Cross-Validation, Leave-one-group-out Cross-Validation, Nested Cross-Validation, or the like to minimize sampling bias and overfitting. Annotation can be performed manually by one or more humans (annotators such as pathologists) confirming characteristics of each dataset and providing labels to the datasets. In some instances, the datasets may be transmitted to an annotator device to be included within a training data set. Input may be provided (e.g., by a pathologist) to the annotator device using (for example) a mouse, track pad, stylus and/or keyboard that indicates (for example) the ground truth result for a given dataset. In some instances, the dataset preparation is referred as obtaining a first set of the filtered datasets as training data. For example, the training data may comprise (i) a set of outcome predictor datasets including historical laboratory test results for subjects that tested abnormal for one or more clinical diagnostic test, and (ii) a set of control datasets including historical laboratory test results for subjects that tested normal for the one or more clinical diagnostic tests. The training data can be annotated with labels corresponding to the set of outcome predictor datasets and set of control datasets as a matrix or table of values. For example, for each predictor or control dataset, an indication of whether a subject tested normal or abnormal for one or more clinical diagnostic test may be provided as ground truth information for labels. The behavior of a model can then be adapted (e.g., through backpropagation) to minimize the difference between the generated inferences and the ground truth information.

The feature engineering includes transforming the datasets (e.g., indexes, outcome predictor datasets, and control datasets) into feature vectors based on filtered features of the datasets. A feature vector is an ordered list of numerical properties of the observed phenomena. The feature vector represents the input features to a machine learning model that makes a prediction based on those features. In some instances, a vector is a sequence of n numbers each of which is indexed by its position in the sequence. Given some number m of objects, each of which is described by an n-component vector, a set of vectors may be organized as an m×n matrix. The indexes, outcome predictor datasets, and control datasets may be translated into vectors and matrices using one or more encoding processes such as one-hot encoding, term frequency-inverse document frequency (TF-IDF), Word2Vec, FastText, and the like, which may be implemented using pre-trained embedding models. A one-hot encoding is a representation of categorical variables as binary vectors. Each integer value is represented as a binary vector that is all zero values except the index of the integer, which is marked with a 1. TF-IDF is a statistical measure used to determine the mathematical significance of words in documents. The vectorization process is similar to one hot Encoding. Alternatively, the value corresponding to the word is assigned a TF-IDF value instead of 1. The TF-IDF value is obtained by multiplying the TF and IDF values. In Word2Vec the entire dataset is scanned, and the vector creation process is performed by determining which words the target word occurs with more often. In this way, the semantic closeness of the words to each other is also revealed. The working logic of FastText algorithm is similar to Word2Vec, but the biggest difference is that it also uses N-grams of words during training. This gives the model the ability to predict different variations of words, The model training includes selecting hyperparameters for the model 135 and using an optimization algorithm (e.g., a stochastic gradient descent algorithm or a variant thereof such as batch gradient descent or minibatch gradient descent) to find the model parameters that correspond to the best fit between predicted and actual outputs. The hyperparameters are settings that can be tuned or optimized to control the behavior of the model 135. Most models explicitly define hyperparameters that control different aspects of the models such as memory or cost of execution. However, additional hyperparameters may be defined to adapt a model to a specific scenario. For example, the hyperparameters may include the number of hidden units of a model, the learning rate of a model, the convolution kernel width, or the number of kernels for a model.

During training, error is calculated as the difference between the actual output and the predicted output. The function that is used to compute this error is known as an objective function (e.g., a loss function or a cost function). Error is a function of internal parameters of the model, e.g., weights and bias. For accurate predictions, the error needs to be minimized. In order to minimize the error, the model parameters are incrementally updated by minimizing the objective function over the training examples. The objective function can be constructed to measure the difference between the outputs inferred using the models and the ground truth annotated to the samples using the labels. For example, for a supervised learning-based model, the goal of the training is to learn a function "h( )" (also sometimes referred to as the hypothesis function) that maps the training input space X to the target value space Y, h: X→Y, such that h(x) is a good predictor for the corresponding value of y. Various different techniques may be used to learn this hypothesis function. In some machine learning algorithms such as a neural network, this is done using back propagation. The current error is typically propagated backwards to a previous layer, where it is used to modify the weights and bias in such a way that the error is minimized. The weights are modified using the optimization function. Optimization functions usually calculate the error gradient, i.e., the partial derivative of the objective function with respect to weights, and the weights are modified in the opposite direction of the calculated error gradient. For example, techniques such as back propagation, random feedback, Direct Feedback Alignment (DFA), Indirect Feedback Alignment (IFA), Hebbian learning, and the like are used update the model parameters in such a manner as to minimize or maximize this objective function. This cycle is repeated until the minima of the objective function is reached.

Once a set of model parameters are identified by the model training, the model 135 has been trained and the validator 134 is configured to validate the model using the validation datasets. The validation process performed by the validator 134 includes iterative operations of inputting the validating datasets into the model 135 using a validation technique such as K-Fold Cross-Validation, Leave-one-out Cross-Validation, Leave-one-group-out Cross-Validation, Nested Cross-Validation, or the like to tune the hyperparameters and ultimately find the optimal set of hyperparameters. Once the optimal set of hyperparameters are obtained, a reserved test set of data from the validating datasets are input into the model 135 to obtain output, and the output is evaluated versus ground truth values using correlation techniques such as Bland-Altman method and the Spearman's rank correlation coefficients and calculating performance metrics such as the error, accuracy, precision, recall, receiver operating characteristic curve (ROC), etc. In some instances, the obtaining, training, and validating data process in the model training subsystem 130 can be repeatedly performed (adjusted) by the trainer 132 and validator 134 until a predetermined condition is satisfied and a set of model parameters can be provided by the model training subsystem 130.

As should be understood, other training/validation mechanisms are contemplated and may be implemented within the system 100. For example, the model 135 may be trained and hyperparameters may be tuned on datasets from the subset of obtained or filtered datasets and the datasets from the subset of obtained or filtered datasets may only be used for testing and evaluating performance of the model 135. Moreover, although the training mechanisms described herein focus on training a new model 135. These training mechanisms can also be utilized to fine tune existing models trained from other datasets. For example, in some instances, a model 135 might have been pre-trained using datasets from different modalities. In those cases, the models 135 can be used for transfer learning and retrained/validated using the training and validating data.

The model training subsystem 130 outputs trained models 135 with an optimized set of model parameters and hyperparameters for use in model inference subsystem 140. The model inference subsystem 140 generates an inference phase prediction using a predictor 142 and the one or more trained models 135. For example, the predictor 142 executes processes for inputting data for a new subject 137 into the one or more trained models 135, generating, using the one or more trained models 135, a prediction based on features extracted from data for the new subject 137, and outputting the prediction. The one or more trained models 135 generate the prediction based on features extracted from the subject's index and historical laboratory test results. In some instances, features of the data for a new subject 137 may be denoised prior to input into the one or more trained models 135, as described herein with respect to data preprocessing subsystem 120. The prediction may be a result or value of a clinical diagnostic laboratory test for the new subject 137. In some instances, a classification is provided for the predicted result or value of a clinical diagnostic test by the predictor 142 based on the output of the one or more trained models 135. For example, the predictor 142 may compare the predicted result or value for the clinical diagnostic laboratory test to a predefined threshold and the predicted result or value is classified as abnormal or normal based on the comparison.

The model inference subsystem 140 outputs the predictor for optional use in analysis subsystem 150. The analysis subsystem 150 comprises one or more analyzers 152 configured for performing analysis based on the prediction or classification output by the model inference subsystem 140 and outputting analysis results 155. In some instances, the one or more analyzers 152 are configured to provide a report for the clinical diagnostic laboratory test based on the prediction or classification output by the model inference subsystem 140. The report may provide information concerning the new subject 137 (e.g., the index and historical laboratory test results) and the prediction or classification output. In some instances, the one or more analyzers 152 are configured to provide a recommendation for the clinical diagnostic laboratory test based on the prediction or classification output. In some instances, the one or more analyzers 152 are configured to administer or perform a clinical diagnostic laboratory test on a sample from the new subject 137 based on the prediction or classification output. In some instances, the prediction and/or analysis results 155 may be used for diagnosing and/or treating the new subject 137. In some instances, the analysis subsystem 150 cooperates or interplays with one or more external system to perform some or all of its analysis functions.

While not explicitly shown, it will be appreciated that the system 100 may further include a developer device associated with a developer. Communications from a developer device to components of the system 100 may indicate what types of input data, measurement data, and/or laboratory test data are to be used for the models, a number and type of models to be used, hyperparameters of each model, for example, learning rate and number of hidden layers, how data requests are to be formatted, which training data is to be used (e.g., and how to gain access to the training data) and which validation technique is to be used, and/or how the controller processes are to be configured.

Figure 2:
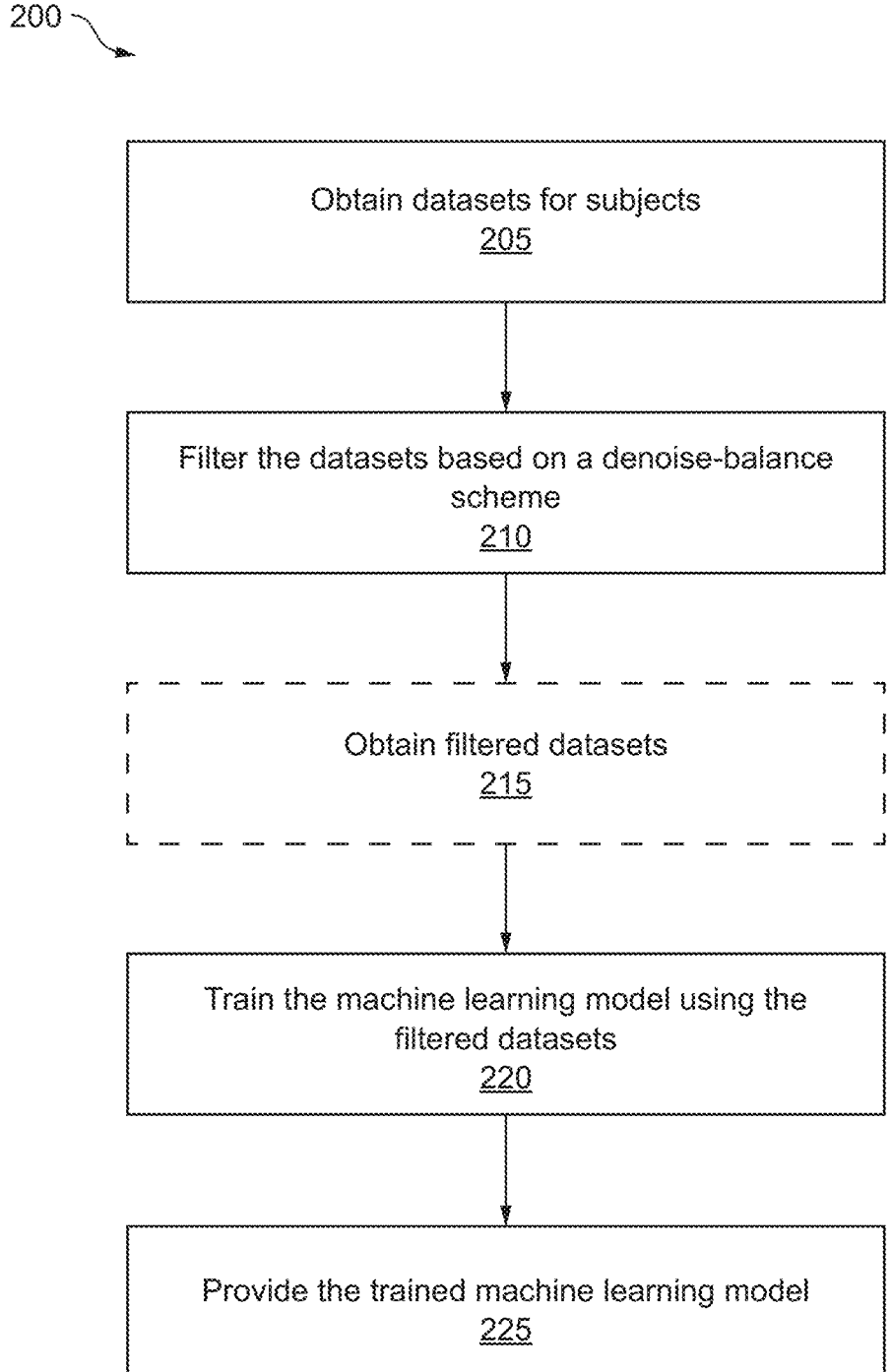
FIG. 2 shows a flowchart illustrating a process for preprocessing datasets and training a machine learning model in accordance with various embodiments.

FIG. 2 is a flowchart illustrating a process 200 for preprocessing datasets and training a machine learning model according to various embodiments. The processing depicted in FIG. 2 may be implemented in software (e.g., code, instructions, program) executed by one or more processing units (e.g., processors, cores) of the respective systems, hardware, or combinations thereof (e.g., the intelligent selection machine). The software may be stored on a non-transitory store medium (e.g., on a memory device). The method presented in FIG. 2 and described below is intended to be illustrative and non-limiting. Although FIG. 2 depicts the various processing steps occurring in a particular sequence or order, this is not intended to be limiting. In certain alternative embodiments, the steps may be performed in some different orders, or some steps may also be performed in parallel. In certain embodiments, the processing or a portion of the processing depicted in FIG. 2 may be performed by system 100 as described with respect to FIG. 1.

At block 205, datasets for subjects are obtained. Each dataset corresponds to one subject, and different datasets may correspond to a same subject. Each dataset comprises subject features such as an index and historical laboratory test results corresponding to test codes. It should be understood that historical laboratory test results corresponding to test codes are not necessarily numerical values. In some embodiments, an index may be a patient identifier, a test date, an age, and/or a gender. In some embodiments, the datasets are acquired from a clinical laboratory or health care system (e.g., analytical chemistry system, hematology system, patient record system, clinical trial testing system, and the like). In some embodiments, the datasets are acquired from a data storage structure such as a database, a laboratory or hospital information system, or the like associated with the one or more modalities for acquiring historical laboratory test results for subjects. In some embodiments, only a subject's most recent laboratory test result corresponding to a test code is obtained. In other embodiments, more than one historical laboratory test results corresponding to a test code are obtained. The more than one historical laboratory test results may be preprocessed based on a denoise-balance scheme illustrated in FIG. 3.

Figure 3:
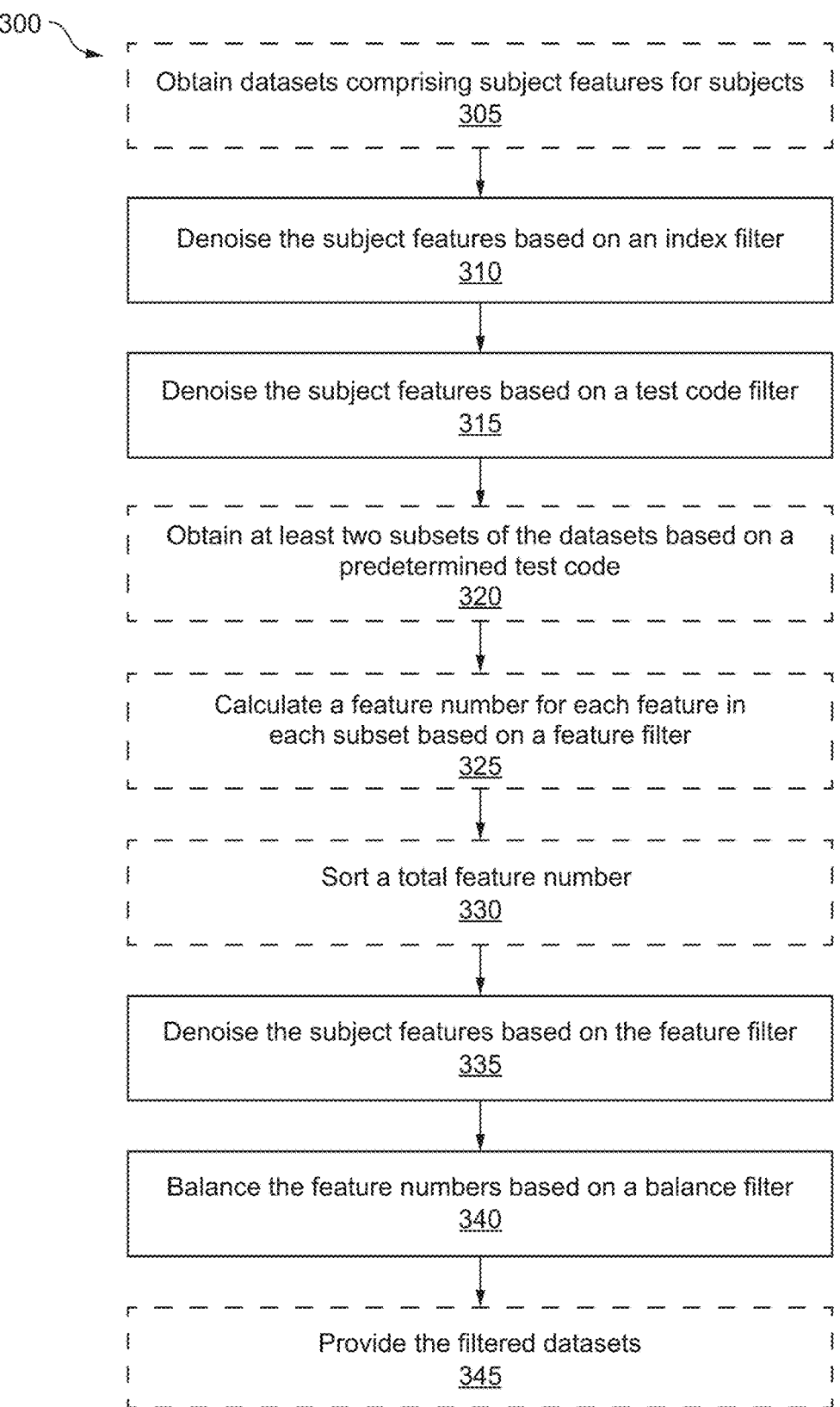
FIG. 3 shows a flowchart illustrating a process for denoising and balancing datasets in accordance with various embodiments.

At block 210, the datasets for the subjects are filtered (denoised and balanced) based on a denoise-balance scheme and filtered datasets are obtained. In some embodiments, the denoise-balance scheme comprises an index filter, a test code filter, a feature filter, and a balance filter. The denoise-balance scheme is illustrated in FIG. 3. This step/block may be referred to as a preprocessing step/block. It should be noted that the techniques regarding denoise and balance the features before training machine learning models result in a substantial improvement in providing accurate predictions on clinical diagnostic test results.

Block 215 is a block that can be performed optionally in the process 200. At block 215, filtered datasets are obtained. In some embodiments, the filtered datasets are for a subset of the subjects ("filtered subjects"). In other words, datasets for a certain group of the subjects are removed from the original datasets. In some embodiments, the filtered datasets for the filtered subjects comprise the index and the historical laboratory test results corresponding to the test codes that are the same as the datasets for the same subjects. In other words, the filtered features in the datasets may be the same as the original features. In other embodiments, the filtered datasets comprise different features than those in the original datasets. In some embodiments, at least some of the filtered datasets may be obtained from an external block other than block 210.

At block 220, a machine learning model is trained using the filtered datasets and a trained machine learning model is obtained. In some embodiments, the performance of the machine learning model is measured based on a prediction of a clinical diagnostic test provided by the machine learning model. One example of the training is further illustrated in FIG. 4.

At block 225, the trained machine learning model is provided. In some embodiments, the performance of the trained machine learning model must meet a predetermined standard to have the trained machine learning model provided. In some embodiments, a set of model parameters is provided together with the trained machine learning model.

FIG. 3 is a flowchart illustrating a process 300 for denoising and balancing datasets according to various embodiments. The processing depicted in FIG. 3 may be implemented in software (e.g., code, instructions, program) executed by one or more processing units (e.g., processors, cores) of the respective systems, hardware, or combinations thereof (e.g., the intelligent selection machine). The software may be stored on a non-transitory store medium (e.g., on a memory device). The method presented in FIG. 3 and described below is intended to be illustrative and non-limiting. Although FIG. 3 depicts the various processing steps occurring in a particular sequence or order, this is not intended to be limiting. In certain alternative embodiments, the steps may be performed in some different orders, or some steps may also be performed in parallel. In certain embodiments, the processing or a portion of the processing depicted in FIG. 3 may be performed by system 100 as described with respect to FIG. 1.

At block 305, datasets comprising subject features for a subject are obtained. The obtaining of the datasets may be the same as the obtaining at block 205 of FIG. 2. In some embodiments, the subject features comprise an index (e.g., patient identifier, a test date, an age, and/or a gender) and historical laboratory test results corresponding to test codes.

At block 310, the subject features are denoised based on an index filter. The denoising may comprise removing a first set of the datasets from the datasets. In some embodiments, a clinical diagnostic test is set to be a target test by the index filter, and a test date for the most recent test result for the target test is marked as an index date. In some embodiments, datasets for subjects with test dates that are earlier than an index date for a certain subject are removed from the datasets by the index filter. In some embodiments, datasets for subjects with test dates that are later than the subjects' own index date are removed from the datasets by the index filter. In some embodiments, datasets for subjects with blank test dates are removed from the datasets by the index filter.

In some embodiments, datasets for subjects with unknown gender are removed by the index filter. In some embodiments, datasets for subjects falling outside of a predetermined age range (e.g., an age range is [18, 90]) are removed by the index filter. In some embodiments, a value of a historical laboratory test result for an earlier test date is reset to a default value by the index filter if a test code of the historical laboratory test result for the earlier test date is the same test code for a later test date. In some embodiments, a value of a historical laboratory test result is reset to a default value by the index filter if a test date for the historical laboratory test result is missing or in an incorrect format or falls outside of a predetermined score range. In some embodiments, a value of a historical laboratory test result is reset to a default value by the index filter if a test date for the historical laboratory test result is prior to a predetermined date. It should be understood that any combination of the hereinbefore and hereinafter embodiments can be performed in any order or in parallel.

At block 315, the subject features are denoised based on a test code filter. The denoising may comprise removing a second set of the datasets from the datasets. In some embodiments, datasets for subjects with a historical laboratory test result for a predetermined test code (e.g., a "skip test" or a "target test") are removed by the test code filter. In some embodiments, datasets for subjects without a historical laboratory test result for a predetermined test code (e.g., a "required test") are removed by the test code filter. In some embodiments, a value of a historical laboratory test result for a predetermined test code for a subject is reset to a default value by the test code filter if the value of a historical laboratory test result for the subject is missing, in an incorrect format, or falls outside of a predetermined score range. In some embodiments, datasets for subjects with a value of a historical laboratory test result are removed by the test code filter if a test date for the historical laboratory test result is later than a predetermined date or a date determined at a prior block.

Blocks 320-330 may be optionally performed according to various embodiments. At block 320, two subsets of the datasets based on a historical laboratory test result corresponding to a predetermined test code are obtained. In some embodiments, more than two subsets of the datasets may be obtained based on a historical laboratory test result corresponding to a predetermined test code. In other embodiments, more than two subsets of the datasets may be obtained based on a historical laboratory test result corresponding to more than one predetermined test codes. In some embodiments, the predetermined test code is a test code for NASH. In some embodiments, the two subsets are obtained based on whether the historical laboratory test result corresponding to the predetermined test code is marked as normal or abnormal. Subjects with normal test results are grouped into a first subset, and subjects with abnormal test results are grouped into a second subset. In some embodiments, datasets for subjects with normal test results are marked as control datasets and datasets for subjects with abnormal test results are marked as outcome predictor datasets. In some embodiments, more than two subsets are obtained because a different endpoint/standard is implemented other than the binary abnormal system. For example, subjects can be grouped based on a low-normal-high endpoint for a test code. Examples may be found in Table 2. In some embodiments, if a dataset for a subject is in two or more subsets, the dataset is removed from each subset.

At block 325, a feature number for each subject feature in each subset of the datasets is obtained based on a feature filter. In some embodiments, a feature number is calculated for each feature in a subset by counting a number of subjects with the feature in the subset by the feature filter. In some embodiments, a ratio of a feature number for a feature in one subset to a feature number for the same feature in another subset is calculated. In some embodiments, it is determined whether the ratio falls in a predetermined ratio scope. In some embodiments, the predetermined ratio scope is about [1:5, 5:1]. In some embodiments, the predetermined ratio scope is [1:5, 5:1]. In some embodiments, if the ratio is not in a predetermined ratio scope, for example, [1:5, 5:1], a number of datasets in one subset is removed from the subset by the feature filter to meet the predetermined ratio scope. In other embodiments, if the ratio is not in the predetermined ratio scope, the feature is removed from the subset by the feature filter.

At block 330, a total feature number is sorted based on the feature filter. In some embodiments, the total feature number equals the sum of the feature number for the same feature in each subset. In some embodiments, the total feature number equals the sum of the feature numbers for the same feature in two or more subsets determined by the feature filter. The sorting may be performed in a descending order, an ascending order, or a predetermined order by the feature filter.

At block 335, the subject features are denoised based on a feature filter. The denoising may comprise removing a third set of the datasets from the datasets. In some embodiments, the feature filter at block 335 is the same filter implemented at blocks 320-330. In some embodiments, a certain number of sorted features are preserved, and the rest are removed from each dataset by the feature filter. The certain number is about 10, 20, 30, 40, 50, 60, 70, 80, 90, 100, 110, 120, 130, 140, or 150. The preserved features may be those with the highest frequency (the greatest total feature number). Datasets with subject features that meet a predetermined level comparing to a total number of preserved features are remained in each subset and datasets not meeting the level are removed by the feature filter. In some embodiments, datasets with subject features that meet a predetermined number are remained in each subset and datasets not meeting the number are removed by the feature filter. The predetermined level is about 5, 10, 15, 20, 25, 30, 35, 40, 45, 50, 55, 60, 65, 70, 75, 80, 85, 90, 95, 100, 110, 120, 130, 140, or 150.

At block 340, the feature numbers are balanced based on a balance filter. The balancing may comprise removing a fourth set of the datasets from the datasets. In some embodiments, a number of datasets for one feature in each subset is determined by the balance filter and a ratio of the number of datasets for the feature in one subset to the number of datasets for the feature in another subset is calculated. In some embodiments, if the ratio is not in a predetermined range, a group of datasets in one subset is removed from the subset by the balance filter to meet the predetermined range. In some embodiments, the predetermined range is 1. In some embodiments, the group of datasets is removed based on a predetermined order. In some embodiments, the removal is based on the frequency of the preserved features in each dataset. In some embodiments, the removal is random. In some embodiments, the balance filter also performs a de-identification function and a combination of subsets function to obtain filtered datasets.

At block 345, the filtered datasets are provided. In some embodiments, the filtered datasets are provided to a machine learning model. The filtered datasets can be used to train and/or to validate the machine learning model. The denoise-balance scheme performed in the process 300 help train machine learning models based on historical laboratory test results and provide more accurate predictions of results for clinical diagnostic tests, comparing with conventional human-intuitive or statistical-based approaches. The denoise-balance scheme as described reduce dimensionality of training data while keeping essential variations to capture the fundamental nature of the data.

In certain embodiments, a denoise-balance scheme is performed according to the following order: (1) compute index date (the index date is the first date at which a subject has an abnormal test result for a clinical diagnostic test to be predicted); (2) filter out null index date (remove datasets for subjects that have a blank index date); (3) filter by index date (remove datasets for subjects with test dates later than the index date); (4) filter skip test and required test (remove features (e.g., test code) from datasets that is identified in a configuration file; (5) filter case/control overlap (removes datasets for subjects that are present in case (abnormal) and control (normal) subsets); (6) filter based on most common test code (for each subset, sum the number of unique test codes and then keep only datasets for subjects that have test codes in both subsets; calculate the ratio between case/count (e.g., 1:5/5:1 ratio); and sum case and control test counts, sort by descending/ascending sum, and keep the top/bottom n (e.g., a number equal to or less than 150) test codes as identified in the configuration file); (7) pivot patient data (for each subject, sort test codes by date and keeps the most recent one, then pivot the test code list to be one subject per row with each column corresponding to a feature; for subject without a test code result, mark the result –1; and count the number of test codes with result values >–1 for each patient and remove subjects with <50% of total number of features); (8) fix class imbalance (random remove subjects to have an equal number in the case and control subsets); (9) label data; and (10) combine case and control subsets into one set.

Figure 4:
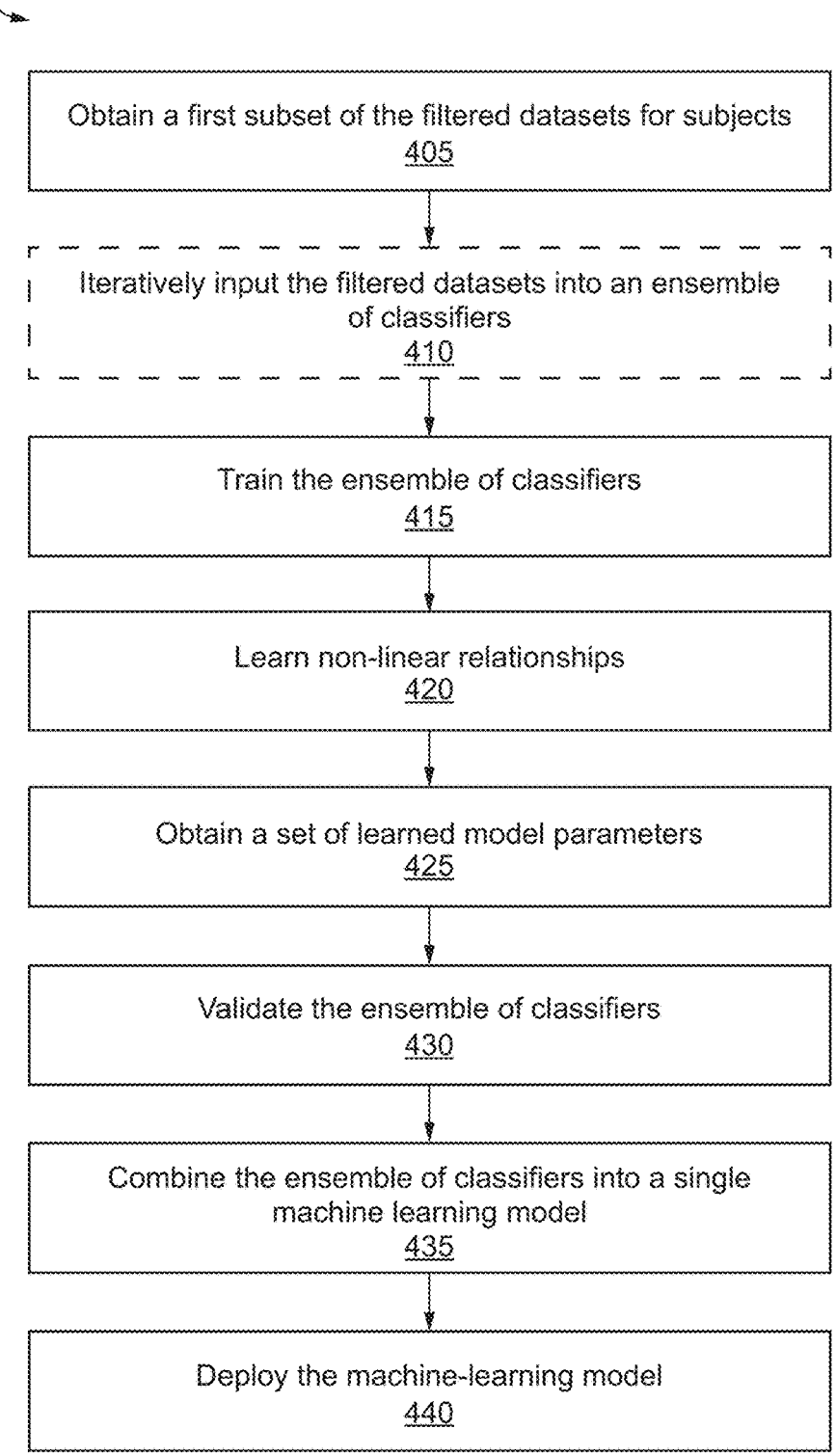
FIG. 4 shows a flowchart illustrating a process for training a machine learning model in accordance with various embodiments.

FIG. 4 is a flowchart illustrating a process 400 for training a machine learning model according to various embodiments. The processing depicted in FIG. 4 may be implemented in software (e.g., code, instructions, program) executed by one or more processing units (e.g., processors, cores) of the respective systems, hardware, or combinations thereof (e.g., the intelligent selection machine). The software may be stored on a non-transitory store medium (e.g., on a memory device). The method presented in FIG. 4 and described below is intended to be illustrative and non-limiting. Although FIG. 4 depicts the various processing steps occurring in a particular sequence or order, this is not intended to be limiting. In certain alternative embodiments, the steps may be performed in some different orders, or some steps may also be performed in parallel. In certain embodiments, the processing or a portion of the processing depicted in FIG. 4 may be performed by system 100 as described with respect to FIG. 1.

At block 405, a first subset of filtered datasets for subjects are obtained as training data. The training data comprise: (i) a set of outcome predictor data including historical laboratory test results for subjects that tested abnormal for one or more clinical diagnostic tests, and (ii) a set of control data including historical laboratory test results for subjects that tested normal for the one or more clinical diagnostic tests. For example, a disease/diagnostic expert may be consulted to identify one or more clinical diagnostic tests to be used for achieving a given task or endpoint. The one or more clinical diagnostic tests may then be used to identify outcome predictor data for subjects that tested abnormal for the one or more clinical diagnostic tests, and identify control data for subjects that tested normal for the one or more clinical diagnostic tests.

In some embodiments, a date on which the abnormal or normal one or more clinical diagnostic tests occurred may be used as determinative of which of the historical laboratory test results are used in block 410 as inputs for training the ensemble of classifiers. In some instances, all of the historical laboratory test results occurring prior to the date on which the abnormal or normal clinical diagnostic test occurred are used as inputs for training the ensemble of classifiers. In certain instances, a predetermine number of most frequent historical laboratory test results for the subjects are selected from the outcome predictor data and the control data and used in block 410 as the training data input into the ensemble of classifiers. The most recent historical laboratory test results may be used for the most frequent historical laboratory test results as the training data input into the ensemble of classifiers. In instances where the historical laboratory test results of a subject are missing one or more historical laboratory test results for the most frequent historical laboratory test results, the one or more historical laboratory test results may be encoded by a predetermined variable. Any historical laboratory test result for the clinical diagnostic test and any historical laboratory test result determined to potentially bias the prediction of the result for the clinical diagnostic test (e.g., indirectly associated with the clinical diagnostic test) may be omitted from the training data. In certain instances, the clinical diagnostic test is a Non-Alcoholic Steatohepatitis (NASH) Fibrosis score test. In other instances, the clinical diagnostic tests are Glomerular filtration rate (eGFR) and ACR (albumin/creatinine ratio). In other instances, the clinical diagnostic test is ACR (albumin/creatinine ratio).

At block 410, the filtered datasets are iteratively input into an ensemble of classifiers implemented with a boosting algorithm. In certain instances, the boosting algorithm is an adaptive boosting algorithm.

At block 415, the ensemble of classifiers is trained by applying base machine learning algorithms on different distributions of the sets of datasets. In some embodiment, the training may comprise three main sub-processes: dataset preparation, feature engineering, and model training. The dataset preparation facilitates the process of loading datasets, splitting the datasets into training and validation, and performing basic machine learning preprocessing functions. The feature engineering includes transforming the datasets (e.g., indexes, outcome predictor datasets, and control datasets) into feature vectors based on filtered features of the datasets. The model training includes selecting hyperparameters and using an optimization algorithm (e.g., a stochastic gradient descent algorithm or a variant thereof such as batch gradient descent or minibatch gradient descent) to find model parameters that correspond to the best fit between predicted and actual outputs.

At block 420, in response to the training, relationships are learned within the filtered dataset that are used by the ensemble of classifiers to predict a result for the one or more clinical diagnostic tests.

At block 425, a set of learned model parameters associated with the relationships is obtained.

At block 430, the ensemble of classifiers is validating by applying the base machine learning algorithms with the set of learned model parameters on different distributions of validating datasets. The validating datasets comprise: (i) a set of outcome predictor test data including historical laboratory test results for subjects that tested abnormal for the one or more clinical diagnostic tests, and (ii) a set of control test data including historical laboratory test results for subjects that tested normal for the one or more clinical diagnostic tests. In some embodiments, the validation process includes iterative operations of inputting the validating datasets into a trained model using a validation technique such as K-Fold Cross-Validation, Leave-one-out Cross-Validation, Leave-one-group-out Cross-Validation, Nested Cross-Validation, or the like to tune the hyperparameters and parameters and ultimately find the optimal set of hyperparameters and parameters.

At block 435, the ensemble of classifiers is combined into a machine learning model having the set of learned model parameters for predicting the result for the one or more clinical diagnostic tests. In some instances, the ensemble of classifiers is combined once a determination is made by the validating that the ensemble of classifiers is capable of achieving a predetermined accuracy for predicting the result for the one or more clinical diagnostic tests. Table 3 demonstrates an example of the filtered features in a trained machine learning model with their corresponding weights (the set of learned model parameters) for predicting NASH fibrosis scores in accordance with various embodiments of the disclosure. It should be understood that the features listed in Table 3 are not the only available features regarding the techniques disclosed herein for training a machine learning model, and they are neither the limited features for predicting NASH fibrosis scores. It should also be understood that the indexes and weights in Table 3 are not intended to be limiting.

result according to various embodiments. The processing depicted in FIG. 5 may be implemented in software (e.g., code, instructions, program) executed by one or more processing units (e.g., processors, cores) of the respective systems, hardware, or combinations thereof (e.g., the intelligent selection machine). The software may be stored on a non-transitory store medium (e.g., on a memory device). The method presented in FIG. 5 and described below is intended to be illustrative and non-limiting. Although FIG. 5 depicts the various processing steps occurring in a particular sequence or order, this is not intended to be limiting. In certain alternative embodiments, the steps may be performed in some different order or some steps may also be performed in parallel. In certain embodiments, the processing or a portion of the processing depicted in FIG. 5 may be performed by system 100 as described with respect to FIG. 1.

At block 505, an index and historical laboratory test results is obtained for a subject.

At block 510, features including the index and/or the historical laboratory test results are input into a machine learning model having a set of model parameters for predicting a result for one or more clinical diagnostic tests. In some embodiments, the machine learning model comprises an ensemble of classifiers, and the set of learned parameters are associated with relationships learned in an unsupervised

TABLE 3

| Index | Feature | Description | Weight |
|---|---|---|---|
| 1 | age | Age | 0.164 |
| 2 | 777-3 | Platelets [#/volume] in Blood by Automated count | 0.124 |
| 3 | 10834-0 | Globulin [Mass/volume] in Serum by calculation | 0.072 |
| 4 | 6768-6 | Alkaline phosphatase [Enzymatic activity/volume] in Serum or Plasma | 0.06 |
| 5 | 785-6 | MCH [Entitle mass] by Automated count | 0.052 |
| 6 | 718-7 | Hemoglobin [Mass/volume] in Blood | 0.036 |
| 7 | 6690-2 | Leukocytes [#/volume] in Blood by Automated count | 0.036 |
| 8 | 788-0 | Erythrocyte distribution width [Ratio] by Automated count | 0.032 |
| 9 | 17861-6 | Calcium [Mass/volume] in Serum or Plasma | 0.028 |
| 10 | 789-8 | Erythrocytes [#/volume] in Blood by Automated count | 0.028 |
| 11 | 2951-2 | Sodium [Moles/volume] in Serum or Plasma | 0.028 |
| 12 | 3094-0 | Urea nitrogen [Mass/volume] in Serum or Plasma | 0.028 |
| 13 | 1751-7 | Albumin [Mass/volume] in Serum or Plasma | 0.028 |
| 14 | 770-8 | Neutrophils/100 leukocytes in Blood by Automated count | 0.028 |
| 15 | 2160-0 | Creatinine [Mass/volume] in Serum or Plasma | 0.024 |
| 16 | 2885-2 | Protein [Mass/volume] in Serum or Plasma | 0.024 |
| 17 | 787-2 | MCV [Entitle volume] by Automated count | 0.024 |
| 18 | 736-9 | Lymphocytes/100 leukocytes in Blood by Automated count | 0.024 |
| 19 | 5905-5 | Monocytes/100 leukocytes in Blood by Automated count | 0.024 |
| 20 | 786-4 | MCHC [Mass/volume] by Automated count | 0.02 |
| 21 | 4544-3 | Hematocrit [Volume Fraction] of Blood by Automated count | 0.016 |
| 22 | 731-0 | Lymphocytes [#/volume] in Blood by Automated count | 0.016 |
| 23 | 711-2 | Eosinophils [#/volume] in Blood by Automated count | 0.012 |
| 24 | 2028-9 | Carbon dioxide, total [Moles/volume] in Serum or Plasma | 0.012 |
| 25 | 1759-0 | Albumin/Globulin [Mass Ratio] in Serum or Plasma | 0.012 |
| 26 | 3097-3 | Urea nitrogen/Creatinine [Mass Ratio] in Serum or Plasma | 0.012 |
| 27 | 2823-3 | Potassium [Moles/volume] in Serum or Plasma | 0.012 |
| 28 | 713-8 | Eosinophils/100 leukocytes in Blood by Automated count | 0.008 |
| 29 | 751-8 | Neutrophils [#/volume] in Blood by Automated count | 0.004 |
| 30 | 706-2 | Basophils/100 leukocytes in Blood by Automated count | 0.004 |
| 31 | 2075-0 | Chloride [Moles/volume] in Serum or Plasma | 0.004 |
| 32 | Gender_M | Male Gender | 0.004 |

At block 440, the machine learning model is deployed. In some embodiments, the machine learning model is deployed to a local computing device. In some embodiments, the machine learning model is deployed at an invocable end point within a cloud infrastructure.

FIG. 5 is a flowchart illustrating a process 500 for using a machine learning model to predict a clinical diagnostic test manner by a boosting algorithm. In some instances, the machine learning model is obtained via the processes described with respect to FIG. 4. In certain instances, the boosting algorithm is an adaptive boosting algorithm.

The machine learning model may be deployed locally or on an invocable end point within a cloud infrastructure, and use of the machine learning model may further comprise invoking, using the end point, the machine learning model via an application programming interface (API).

At block 515, the result for the one or more clinical diagnostic tests is predicted using the machine learning model. The prediction may provide a value and/or a classification for the one or more clinical diagnostic tests.

At block 520, a classification and/or assessment of the one or more clinical diagnostic tests is output based on the predicted result for the one or more clinical diagnostic tests. The classification of the one or more clinical diagnostic tests may comprise comparing the result for the one or more clinical diagnostic tests to a determined threshold and classifying the one or more clinical diagnostic tests as abnormal or normal based on the comparison.

At block 525, a recommendation for the one or more clinical diagnostic tests is provided based on the classification of the one or more clinical diagnostic tests. In some instances, the recommendation is provided to a user such as a clinician (e.g., a health care worker associated with the subject).

At block 530, the one or more clinical diagnostic tests are performed, or performance is facilitated, on a sample from the subject to obtain an analytical result for the one or more clinical diagnostic tests.

At block 535, the subject is diagnosed and/or treated based on the analytical result and/or the classification or assessment for the one or more clinical diagnostic tests.

III. EXAMPLES

The models and techniques implemented in various embodiments may be better understood by referring to the following examples.

Example 1: Predicting Non-Alcoholic Steatohepatitis (NASH) Fibrosis from Patient Laboratory Testing History Introduction Non-alcoholic fatty liver disease (NAFLD) is the most common chronic liver disease worldwide (Younossi et al. 2020). It is a spectrum of liver disease characterized by hepatic steatosis, i.e. excess lipid accumulation in hepatocytes, without evidence of hepatocellular injury in the absence of excessive alcohol use. In the United States, NAFLD prevalence is 25-30% and is expected to increase, becoming the leading cause of liver transplantation between 2020-2025 (Wong et al. 2015; Le et al. 2017). Most NAFLD patients have simple steatosis, i.e. accumulation of fat in the liver, a condition commonly associated with metabolic comorbidities including type 2 diabetes (T2D), hypertension, metabolic syndrome, obesity, and hyperlipidemia (Younossi et al. 2016). About 25-30% of adults in the United States have NAFLD; 5-6% go on to develop non-alcoholic steatohepatitis (NASH) (Diehl and Day 2017). NAFLD/ NASH is often asymptomatic and even when symptoms develop, they are frequently non-specific symptoms such as malaise, fatigue, and/or vague abdominal pain. NASH is characterized by inflammation, cell death and hepatocellular damage (e.g. ballooning), with or without fibrosis (Browning and Horton 2004; Brunt et al. 2011; Chalasani et al. 2018). The inflammation and liver damage of NASH can cause liver fibrosis, or scarring (Younossi et al. 2011; Angulo et al. 2015; Ekstedt et al. 2015), and may lead to cirrhosis and permanent damage to the liver.

The gold standard for diagnosis and staging of NASH is liver biopsy (Chalasani et al. 2018; Wong et al. 2015), which is an invasive procedure that comes with associated risks, including pain and bleeding (Rockey et al. 2009), as well as additional costs. Lifetime direct medical costs for NASH patients in the United States in 2017 were estimated at \$222 billion (Younossi, Tampi, et al. 2019). Although NASH severity is associated with higher healthcare resource utilization (HCRU) and cost (Gordon et al. 2020), it remains a largely underdiagnosed disease (Alqahtani et al. 2021; Wessels and Rosenberg 2021), highlighting the need for both automated and early detection.

A recent systematic review of AI applications in NAFLD identified 37 published articles; most used imaging techniques or digital pathology (Popa et al. 2021). Only seven used tabular health data (i.e. electronic health records), and only one was used to predict NASH in NAFLD patients (Fialoke et al. 2018). Even more recent AI approaches for NASH have been trained on small datasets (e.g. fewer than 1,000 patients) with minimal features using histologically diagnosed NAFLD or NASH (Docherty et al. 2021; Okanoue et al. 2021a; 2021b).

As liver biopsy for NASH screening in the general population is not feasible, the objective of the following study was to develop a machine learning (ML) model for early identification of NASH patients using real-world laboratory testing data from a US-based national reference laboratory (Labcorp). Herein is describe the development of a ML model that predicts the result of a NASH fibrosis score test based on patient laboratory testing history to accurately identify patients trending towards an abnormal diagnostic test result and to support clinicians and healthcare organizations by potentially informing diagnosis early.

Methods

Patient Data

Patients that took a Labcorp NASH FibroSure® test (550140) between Jan. 1, 2011 and Apr. 29, 2021 with fibrosis scores greater than 0.31 (METAVIR scoring system fibrosis stage F1-F2 and higher) were the outcome predictor that the model was tasked with predicting, whereas patients with a fibrosis score less than or equal to 0.31 and never having a fibrosis score greater than 0.31 were used as controls (Ratziu et al. 2006; Poynard et al. 2021; Munteanu et al. 2016; Vali et al. 2021; Bril et al. 2019). Patient testing histories were truncated using the patient's first fibrosis score greater than 0.31 for cases and the first fibrosis score less than or equal to 0.31 for controls. The date on which the first fibrosis score of interest occurred dictated which test results were used as inputs for the model. All test results occurring prior to the date of interest were considered; the 150 most frequent diagnostic tests performed within the cohort were selected as inputs for the model. For each patient, the most recent test result for each of the 150 top test results were used as inputs; missing or cases where a patient was not tested for a given test was accounted for in the model by encoding those variables as −1. If the patient had multiple occurrences of the same test before the date of interest, the most recent result was chosen.

Model Training

The model was trained and deployed using Amazon Web Services (AWS) SageMaker, Python 3.7, and Scikit-Learn. An Adaptive Boosting (AdaBoost) model (Freund and Schapire 1999) was trained to predict a NASH fibrosis score result (Logical Observation Identifiers Names and Codes (LOINC) result code 48795-9) using 250 estimators and five k-fold cross validation. Of the top 150 tests used as inputs, the final model determined 97 to be important as features. To prevent liver fibrosis status from patient histories guiding model predictions, all other result codes from the NASH FibroSure® test (550140) were omitted from model evaluation, as well as all result codes from the ASH FibroSure® test (550180) and the Hepatitis C Virus (HCV) FibroSure® test (550123). Additionally, six LOINC result codes for liver fibrosis score calculated by methods other than FibroSure® were omitted. The model predicted a binary output with one being abnormal and zero being normal. The NASH fibrosis score model was trained on laboratory testing histories from 62,001 Labcorp patients and tested on histories from 20,642 Labcorp patients.

Model Deployment

The NASH fibrosis score model was deployed to an invocable endpoint through AWS SageMaker. The model is persisted in SageMaker and can be invoked for real time predictions. SageMaker batch transform provides additional functionality to get inferences on large cohorts.

Inference

A cohort of Labcorp patients independent of those used for model training/testing (i.e. fibrosis score test result naïve) were scored using the NASH fibrosis score model. The cohort of patients consisted of any patient who had received a Labcorp test in the past year (i.e. between Jul. 1, 2020 and Jul. 1, 2021) but never received a fibrosis score test result. Each patient's test history was then queried to find the most recent test, if available, for each of the 97 tests used as inputs for the model. SageMaker batch transform was used for inference on the cohort; each patient received a score that identified them as either predicted fibrosis score normal or abnormal.

Geographic Surveillance of Potential Disease

Geographic mapping was developed in Amazon SageMaker using python 3.7 with geopands and plotly. Test patients scored from the NASH fibrosis model were sorted into abnormal and normal based on a threshold of 0.503127 (which corresponds to 84.6% PPV and 90.4% NPV). Abnormal patients were then grouped by 5-digit zip code and the log count of abnormal patients within each zip code plotted onto a map of the U.S. (zip code boundaries used by geopandas were obtained from the U.S. Census bureau).

Clinical Calibration

Two cohorts of Labcorp patients, either diagnosed or never diagnosed with T2D in the past year (i.e. between Jul. 1, 2020 and Jul. 1, 2021), were generated and used to create a 2×2 contingency table consisting of the following groups: fibrosis score predicted abnormal, fibrosis score predicted normal, T2D diagnosed, T2D never diagnosed. A chi-square test was performed to evaluate association between the groups.

Results

Experimental Model Results

Our initial cohorts consisted of 68,627 patients with a positive/abnormal fibrosis score (i.e. cases) and 70,801 patients with a negative/normal fibrosis score (i.e. controls). The mean±standard deviation (SD) age for the cases cohort was 63.0±11.9; gender distribution was 40.3% females and 59.7% males. For the controls cohort, the mean±SD age was 51.9±13.8, consisting of 62.5% females and 37.5% males. The most recent abnormal or normal fibrosis score date (i.e. index date) was identified for case and control cohorts, respectively, and used for patient matching (FIG. 1). After preprocessing, a total of 82,643 patients were randomly split into training (62,001) and testing (20,642) datasets. FIG. 6. shows example of how test data is preprocessed. The heavier solid line identifies the patient's most recent NASH abnormal or normal fibrosis score date (index date). Tests after the index date are excluded from model inputs.

Feature/Biomarker Importance

Logical Observation Identifiers Names and Codes (LOINC) is clinical terminology that is important for laboratory test orders and results, and is a designated standard for use in U.S. Federal Government systems for the electronic exchange of clinical health information. LOINC result codes were used for model features to provide wide applicability and compatibility across different labs. The 150 most frequent test LOINC result codes were identified from the training cohort and used as inputs for the model. The AdaBoost algorithm from the Python Scikit-Learn library assigns a weight to each training item according to the Gini importance, computed as the (normalized) total reduction of the criterion brought by that feature. After training, 97 LOINC result codes were used as features by the model to predict a fibrosis score result. To better understand the biomarkers represented by each feature, LOINC result codes were mapped to LOINC components (i.e. the substance or entity being measure or observed); the top 20 LOINC component/result code features are shown in Table 4.

TABLE 4

Top 20 model LOINC component (LOINC code) features, rank and feature importance Antigen (ag), high-density lipoprotein (HDL), low-density lipoprotein (LDL), very-low-density lipoprotein (VLDL).

| LOINC component (LOINC code) | Rank | Feature importance |
|---|---|---|
| Bilirubin.glucuronidated + Bilirubin.albumin bound (1968-7) | 1 | 6.80% |
| Platelets (777-3) | 2 | 6.80% |
| Aspartate aminotransferase (AST) (1920-8) | 3 | 6.40% |
| Erythrocyte mean corpuscular hemoglobin (785-6) | 4 | 3.60% |
| Cholesterol.in HDL (2085-9) | 5 | 3.60% |
| Alanine aminotransferase (ALT) (1742-6) | 6 | 3.60% |
| Glomerular filtration rate/1.73 sq M.predicted.non black (48642-3) | 7 | 3.20% |
| Coagulation tissue factor induced (5902-2) | 8 | 2.80% |
| Glomerular filtration rate/1.73 sq M.predicted.non black (88294-4) | 9 | 2.40% |
| Alkaline phosphatase (ALP) (6768-6) | 10 | 2.40% |
| Cholesterol.in LDL (13457-7) | 11 | 2.40% |
| Albumin (1751-7) | 12 | 2.40% |
| Creatinine (2160-0) | 13 | 2.00% |
| Prostate specific Ag (2857-1) | 14 | 2.00% |
| Erythrocyte distribution width (788-0) | 15 | 2.00% |
| Cholesterol.in VLDL (13458-5) | 16 | 1.60% |
| Globulin (10834-0) | 17 | 1.60% |
| Glomerular filtration rate/1.73 sq M.predicted.black (88293-6) | 18 | 1.60% |
| Glomerular filtration rate/1.73 sq M.predicted.black (48643-1) | 19 | 1.20% |
| Hemoglobin A1c/Hemoglobin.total (4548-4) | 20 | 1.20% |

Bilirubin, a compound that is made during the normal breakdown of red blood cells, and platelets, blood cells that play a central role in primary hemostasis by forming aggregates when they recognize damaged blood vessels, had the most importance at 6.80% each. Many of the top 20 features are also used as biomarkers to evaluate liver or kidney function, including bilirubin, albumin, alanine aminotransferase (ALT), aspartate aminotransferase (AST), alkaline phosphatase (ALP), creatinine, and glomerular filtration rate. Several hemoglobin and/or erythrocyte markers (erythrocyte mean corpuscular hemoglobin, erythrocyte distribution width, and hemoglobin A1c/hemoglobin total) are also present in the top 20 features. Lastly, the cholesterol content of the various lipoprotein classes (HDL, LDL, and VDL)

was also identified as being important for predicting which patients have NASH with liver fibrosis.

In training and testing cohorts, mean and standard deviation were calculated for both case and control population top 20 model features (Table 5). A t-test for each of the top 20 model features shows that all mean test result differences were significantly different (p-value<0.05).

TABLE 5

Mean, standard deviation and p-values for the top 20 model features (LOINC components).

| LOINC component (LOINC code) | Mean value ± standard deviation | | |
| --- | --- | --- | --- |
| | Cases (N = 39916) | Controls (N = 42727) | T-Test P-value |
| Bilirubin.glucuronidated + Bilirubin.albumin bound (1968-7) | 0.28 ± 0.74 | 0.13 ± 0.17 | 2.22e–030 |
| Platelets (777-3) | 206.41 ± 75.76 | 270.09 ± 70.52 | 0.00e+000 |
| Aspartate aminotransferase (AST) (1920-8) | 55.32 ± 56.51 | 37.74 ± 37.49 | 0.00e+000 |
| Erythrocyte mean corpuscular hemoglobin (785-6) | 30.4 ± 2.6 | 29.41 ± 2.29 | 6.43e–011 |
| Cholesterol.in HDL (2085-9) | 46.76 ± 15.87 | 51.65 ± 16.17 | 3.74e–168 |
| Alanine aminotransferase (ALT) (1742-6) | 59.88 ± 65.38 | 49.64 ± 51.06 | 3.70e–061 |
| Glomerular filtration rate/1.73 sq M.predicted.non black (48642-3) | 81.79 ± 19.85 | 91.77 ± 19.2 | 3.06e–055 |
| Coagulation tissue factor induced (5902-2) | 12.51 ± 5.32 | 10.95 ± 2.8 | 9.80e–161 |
| Glomerular filtration rate/1.73 sq M.predicted.non black (88294-4) | 78.79 ± 21.27 | 89.53 ± 20.03 | 2.14e–180 |
| Alkaline phosphatase (ALP) (6768-6) | 105.34 ± 78.52 | 88.32 ± 39.72 | 5.76e–118 |
| Cholesterol.in LDL (13457-7) | 93.53 ± 37.57 | 107.34 ± 35.44 | 3.63e–251 |
| Albumin (1751-7) | 4.25 ± 0.44 | 4.41 ± 0.33 | 3.55e–109 |
| Creatinine (2160-0) | 0.98 ± 0.55 | 0.86 ± 0.38 | 1.13e–014 |
| Prostate specific Ag (2857-1) | 1.53 ± 2.86 | 1.6 ± 13.19 | 7.60e–072 |
| Erythrocyte distribution width (788-0) | 14.28 ± 1.64 | 14 ± 1.26 | 2.77e–024 |
| Cholesterol.in VLDL (13458-5) | 29.18 ± 15.5 | 29.42 ± 14.82 | 1.30e–013 |
| Globulin (10834-0) | 2.87 ± 0.59 | 2.69 ± 0.43 | 1.39e–003 |
| Glomerular filtration rate/1.73 sq M.predicted.black (88293-6) | 91.04 ± 24.55 | 103.37 ± 23.09 | 1.30e–180 |
| Glomerular filtration rate/1.73 sq M.predicted.black (48643-1) | 94.55 ± 22.9 | 105.96 ± 22.13 | 6.98e–055 |
| Hemoglobin A1c/Hemoglobin.total (4548-4) | 6.6 ± 1.52 | 6.22 ± 1.31 | 8.53e–019 |

NASH Fibrosis Model Performance

Figure 7:
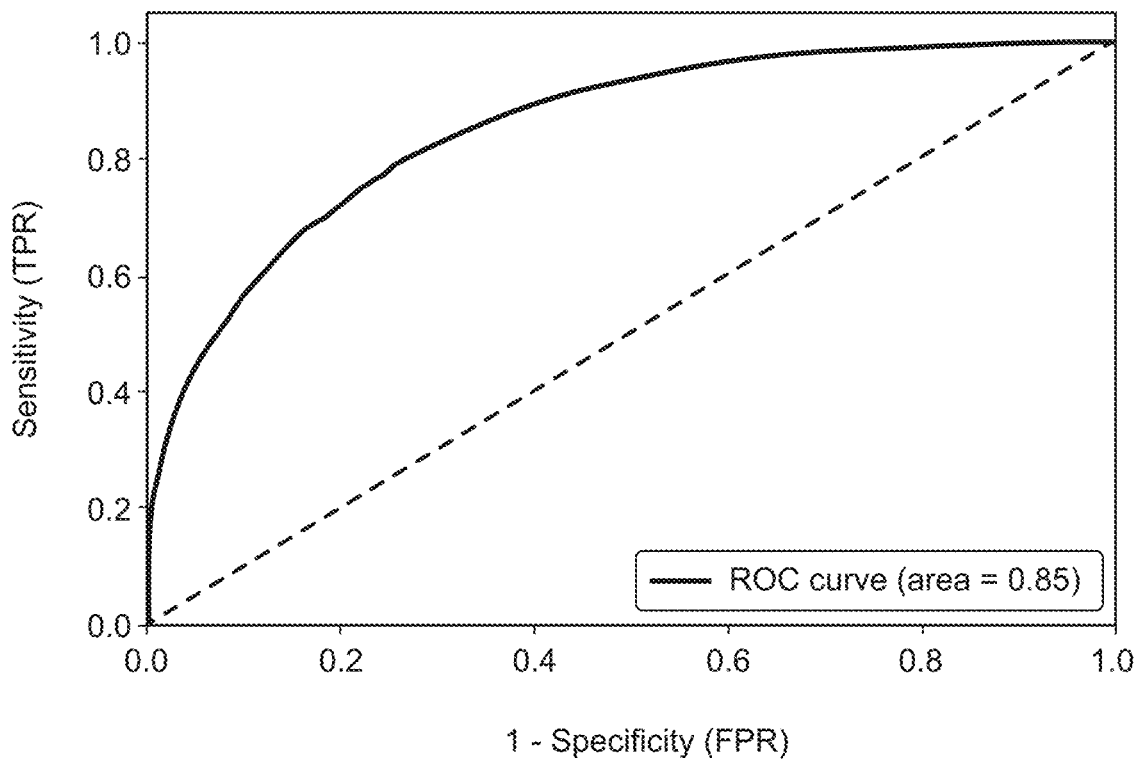
FIG. 7 shows model performance in Non-Alcoholic Steatohepatitis (NASH) Fibrosis prediction in accordance with various embodiments.

The NASH fibrosis model demonstrated high performance as measured by area under the curve (AUC=0.85) on a holdout testing cohort of 20,642 Labcorp patients (FIG. 7). FIG. 7 shows model performance in NASH liver fibrosis prediction. Receiver operating characteristic (ROC), true abnormal rate (TRP), false abnormal rate (FPR). At a threshold score of 0.503127358, the NASH fibrosis model exhibited 22.7% sensitivity, 99.4% specificity, 84.6% abnormal predictive value (PPV), and 90.4% normal predictive value (NPV). The model also had a cross-validated AUC (CV-AUC) of 0.85.

Geographic Surveillance of Potential Disease

Figure 8:
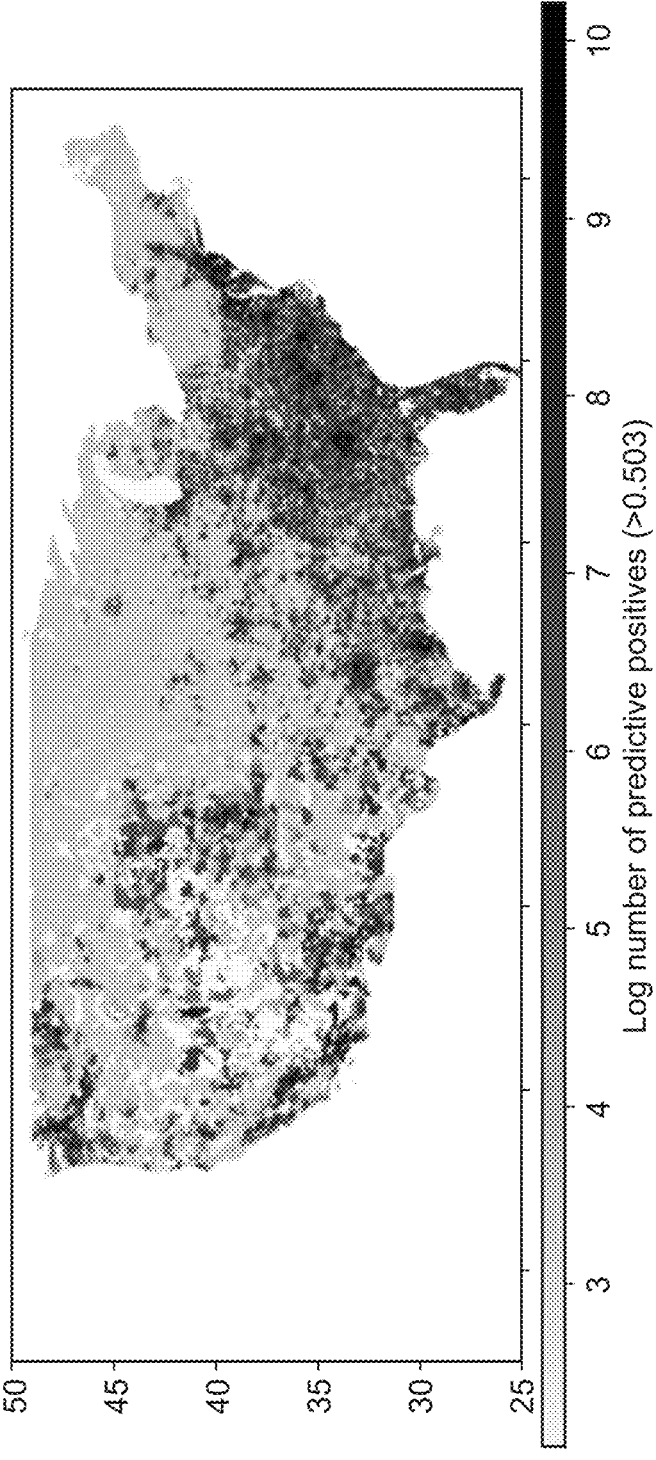
FIG. 8 shows the log count of predicted abnormal NASH Labcorp patients in U.S. zip codes in accordance with various embodiments.

The NASH fibrosis model was used for inference in a Fibrosis score test result naïve cohort of patients. Over 80 million patients (80,020,739) received a Labcorp test in the last year but never received a fibrosis score test result. Batch transform was used to score each patient with the NASH fibrosis model; 16 million patients (16,063,347) were predicted to have an abnormal Fibrosis score test result. The log count of predicted abnormal Fibrosis score test result patients were visualized against U.S. zip codes (FIG. 8). FIG. 8 shows log count of predicted abnormal fibrosis score test result Labcorp patients in U.S. zip codes.

Clinical Collaboration

Several studies have shown that diabetes risk and T2D are closely associated with NAFLD severity, progression to NASH, advanced fibrosis, and the development of hepatocellular carcinoma (Vernon, Baranova, and Younossi 2011; Loomba et al. 2012; Anstee, Targher, and Day 2013). To evaluate the overlap between patients predicted to have NASH liver fibrosis and T2D, four new patient cohorts were created: two based on their status of T2D diagnosis in the past year (i.e. between Jul. 1, 2020 and Jul. 1, 2021), either diagnosed with T2D or never diagnosed with T2D, and two based on NASH fibrosis prediction, either predicted normal or abnormal. A chi-square test demonstrated that there is a significant association between T2D diagnosis and NASH liver fibrosis prediction (odds ratio=2.821; 95% confidence interval=2.816, 2.826), indicating that patients diagnosed with T2D were almost 3 times as likely to be identified as likely having NASH liver fibrosis by our model than patients never diagnosed with T2D. This is consistent with a report that the global prevalence of NASH among individuals with T2D was 37.3% (Younossi, Golabi, et al. 2019).

Discussion

Described herein is a comprehensive ML model for the prediction of NASH liver fibrosis defined non-invasively by FibroSure® test. The model was trained and tested in NASH fibrosis score abnormal and normal patients (as defined by a NASH FibroTest score of > or <0.31) and clinically calibrated by showing a significant association with T2D diagnosis for those patients who were abnormally identified using the NASH fibrosis prediction model. Our 97 feature model achieved high performance, specificity, PPV, and NPV to predict the presence of NASH with liver fibrosis (i.e. an abnormal fibrosis score) and represents a performant, non-invasive method for NASH screening.

Experimental Model Limitations

There are several limitations to our NASH fibrosis model. It is equally benefited and handicapped by the presence of tests in a patient's history. During training, the model imposes no requirements on the number of tests a patient must have to be included in the cohort. At inference, there is also no minimum number of tests a patient must have since the model the training cohort included similar patients. The low sensitivity may mean that it will miss patients that would score abnormal on a NASH Fibrosis score test. However, the high specificity allows for high confidence in the patients the model predicts as abnormal and helps to minimize physician alert fatigue. The low sensitivity and high specificity are not concerning for the application of this model since the goal is early detection. In practice, an abnormal output from the model should be confirmed using more definitive diagnostic testing for NASH with liver fibrosis.

Feature/Biomarker Importance

Glucuronidated bilirubin, albumin-bound bilirubin, and platelet count were the most important biomarkers used by the NASH fibrosis model. During bilirubin hemostasis, albumin-bound bilirubin in the blood is taken up by hepatocytes where glucuronidation occurs via UDP-glucuronosyltransferases. Glucuronidation of bilirubin in the liver is the key event for its subsequent elimination from the human body. In our data, albumin-bound and glucuronidated bilirubin mean results increased in cases vs. controls; according to guidelines by the American College of Gastroenterology (ACG), elevated conjugated bilirubin implies hepatocellular disease or cholestasis (Kwo, Cohen, and Lim 2017). In contrast, a decrease in mean platelet count was observed in cases vs. controls, consistent with reports of decreased platelet count with increasing histologic severity of hepatic fibrosis or odds of cirrhosis (Yoneda et al. 2011; Gotlieb et al. 2020).

A number of liver and kidney function biomarkers were identified by the NASH fibrosis score model. Consistent with other published reports, alanine aminotransferase (ALT), aspartate aminotransferase (AST), alkaline phosphatase (ALP), and creatinine were all increased in cases vs. controls. Elevations of AST and/or ALT, ALP, and bilirubin (above) are recognized to suggest hepatocellular injury (Kwo, Cohen, and Lim 2017). Mean albumin result values decreased in cases vs. controls. Decreased albumin is observed in liver disease and is roughly proportional to the reduction in liver synthesis rates (Levitt and Levitt 2016). Mean creatinine result values increased in cases vs. controls. Creatinine is a break down product of creatine phosphate and is the result of normal muscle metabolism. With liver disease, poor liver function interferes with creatine phosphate production, which can cause low creatinine.

A decrease in mean glomerular filtration rate was observed in cases vs. controls. Several studies have shown that the prevalence of NAFLD is increased in patients with reduced glomerular filtration rate (Targher et al. 2010; Sirota et al. 2012; Adams et al. 2017).

Several hemoglobin and/or erythrocyte markers were increased in cases vs. controls, including erythrocyte mean corpuscular hemoglobin (MCH), erythrocyte distribution width, and hemoglobin A1c/total hemoglobin. MCH is an estimate of the amount of hemoglobin in an average red blood cell. Hemoglobin concentration has been shown to be a risk marker of both NAFLD and metabolic syndrome (Chung et al. 2017) and elevated hemoglobin is also associated with advanced fibrosis in pediatric NAFLD (Giorgio et al. 2017). Erythrocyte distribution width (abbreviated RDW for red cell distribution width) is a measure of the size inconsistency of circulating red blood cells or erythrocytes. RDW is closely associated with NAFLD (Yang et al. 2014).

Consistent with the observed increase in hemoglobin A1c/total hemoglobin in cases vs. controls, a recent study found that higher plasma A1c was associated with a greater prevalence of NAFLD in T2D patients (Portillo-Sanchez et al. 2015), and a significant association between T2D diagnosis and NASH fibrosis prediction was demonstrated.

Cholesterol has been shown to contribute to NASH pathogenesis (Alkhouri, Dixon, and Feldstein 2009). Lipotoxicity (i.e. the accumulation of lipid intermediates in non-adipose tissue) drives the development of progressive hepatic inflammation and fibrosis, causing NASH and progression to cirrhosis and hepatocellular carcinoma. It may be that the decreases in serum HDL, LDL and VLDL cholesterol are due to an accumulation of cholesteryl esters in the liver, or it may be a function of poor lipoprotein metabolism due to the reduction in circulating lipases that often occurs in liver disease.

NASH Fibrosis Model Performance

For this study, the prevalence of NASH in the United States (12%) was used to calculate the PPV and NPV. However, the prevalence of abnormal fibrosis score is likely higher and as such, the PPV and NPV may be underestimated. Using Labcorp data, the prevalence of an abnormal NASH fibrosis score was calculated to be 33.3%, which if extended to the training/testing cohort gives a PPV and NPV of 95.5% and 71.0% respectively.

Geographic Surveillance of Potential Disease

Our inference in a fibrosis score test result naïve cohort of patients was limited by Labcorp geographic coverage, as well as patient access due to insurance coverage. Nevertheless, the log count of predicted abnormal fibrosis score test result patients against U.S. zip codes highlights the degree of underdiagnoses for NASH.

Conclusion

Early detection of NASH allows for interventions to prevent progression and subsequently reduce HCRU and costs. The NASH fibrosis model is a convenient, predictive tool for clinicians and healthcare organizations to identify patients with potentially undiagnosed NASH liver fibrosis. Patients identified should have a more extensive work up in order to confirm the presence of NASH with liver fibrosis. The NASH fibrosis model thus allows for early detection and enhanced patient care.

Example 2: An Alternative Approach for Predicting Non-Alcoholic Steatohepatitis (NASH) Fibrosis from Patient Laboratory Testing History The techniques described herein include preprocessing methods to denoise and balance samples before training a machine learning model to predict clinical diagnostic tests. In addition to Example 1, Example 2 descripts an example of preprocessing samples before training a machine learning model to predict NASH fibrosis scores. The initial samples consisted of 76,687 patients with an abnormal fibrosis score (i.e., cases) and 157,203 patients with a normal fibrosis score (i.e., controls). An index filter is executed to exclude 28,160 control samples. The samples are further denoised and balanced based on a test code filter, a feature filter, and a balance filter. 36,444 case samples and 36,444 control samples (i.e., filtered datasets) are obtained after the preprocessing with 32 filtered features. A training of machine learning models based on an ensembled method is performed and the performance of the training is listed in Table 6 below.

TABLE 6

| Clinical Diagnostic Test | # Features | n-test | AUC | CV-AUC | Test AUC |
|---|---|---|---|---|---|
| NASH fibrosis score | 32 | 18,093 | 0.883 | 0.874 | 0.877 |

A comparison of machine learning model performance can be found in Table 7 below. From the table it can be found that preprocessing of samples help improve the CV-AUC score, which demonstrates improvement in providing trained machine learning models, and also a potential for accurate prediction regarding a clinical diagnostic test.

TABLE 7

| Clinical Diagnostic Test | CV-AUC |
|---|---|
| NASH fibrosis score prediction (previous preprocessing) | 0.804 |
| NASH fibrosis score prediction (updated preprocessing using techniques described in this application) | 0.846 |

Example 3: Predicting Other Clinical Diagnostic Tests from Patient Laboratory Testing History Examples 1 and 2 shows examples of predicting NASH fibrosis scores using the techniques described herein. The techniques can be used in other clinical diagnostic tests, for example, in Albumin/Creatinine Ratio (ACR) for detecting early kidney disease in people with diabetes or other risk factors, such as high blood pressure (hypertension), or in Chronic Kidney Disease (CKD) prediction. Table 8 shows two examples of machine learning model performance using the techniques described herein regarding ACR and CKD.

TABLE 8

| Clinical Diagnostic Test | # Features | CV-AUC |
|---|---|---|
| ACR | 30 | 0.68 |
| CKD | 150 | 0.82 |

REFERENCES

Adams, Leon A, Quentin M Anstee, Herbert Tilg, and Giovanni Targher. 2017. "Non-Alcoholic Fatty Liver Disease and Its Relationship with Cardiovascular Disease and Other Extrahepatic Diseases." Gut 66 (6): 1138-53. https://doi.org/10.1136/gutjnl-2017-313884.

Alkhouri, Naim, Laura J Dixon, and Ariel E Feldstein. 2009. "Lipotoxicity in Nonalcoholic Fatty Liver Disease: Not All Lipids Are Created Equal." Expert Review of Gastroenterology & Hepatology 3 (4): 445-51. https://doi.org/10.1586/egh.09.32.

Alqahtani, Saleh A., James M. Paik, Rakesh Biswas, Tamoore Arshad, Linda Henry, and Zobair M. Younossi. 2021. "Poor Awareness of Liver Disease Among Adults With NAFLD in the United States." Hepatology Communications 0 (0): 1-3. https://doi.org/10.1002/hep4.1765.

Angulo, Paul, David E. Kleiner, Sanne Dam-Larsen, Leon A. Adams, Einar S. Bjornsson, Phunchai Charatcharoenwitthaya, Peter R. Mills, et al. 2015. "Liver Fibrosis, but No Other Histologic Features, Is Associated With Long-Term Outcomes of Patients With Nonalcoholic Fatty Liver Disease." Gastroenterology 149 (2): 389-397.e10. https://doi.org/10.1053/j.gastro.2015.04.043.

Anstee, Quentin M., Giovanni Targher, and Christopher P. Day. 2013. "Progression of NAFLD to Diabetes Mellitus, Cardiovascular Disease or Cirrhosis." Nature Reviews Gastroenterology & Hepatology 10 (6): 330-44. https://doi.org/10.1038/nrgastro.2013.41.

Bril, Fernando, Michael J. McPhaul, Michael P. Caulfield, Jean Marie Castille, Thierry Poynard, Consuelo Soldevila-Pico, Virginia C. Clark, Roberto J. Firpi-Morell, Jinping Lai, and Kenneth Cusi. 2019. "Performance of the SteatoTest, ActiTest, NashTest and FibroTest in a Multiethnic Cohort of Patients with Type 2 Diabetes Mellitus." Journal of Investigative Medicine 67 (2): 303-11. https://doi.org/10.1136/jim-2018-000864.

Browning, Jeffrey D., and Jay D. Horton. 2004. "Molecular Mediators of Hepatic Steatosis and Liver Injury." Journal of Clinical Investigation 114 (2): 147-52. https://doi.org/10.1172/JCI200422422.

Brunt, Elizabeth M., David E. Kleiner, Laura A. Wilson, Patricia Belt, and Brent A. Neuschwander-Tetri. 2011. "Nonalcoholic Fatty Liver Disease (NAFLD) Activity Score and the Histopathologic Diagnosis in NAFLD: Distinct Clinicopathologic Meanings." Hepatology 53 (3): 810-20. https://doi.org/10.1002/hep.24127.

Chalasani, Naga, Zobair Younossi, Joel E. Lavine, Michael Charlton, Kenneth Cusi, Mary Rinella, Stephen A. Harrison, Elizabeth M. Brunt, and Arun J. Sanyal. 2018. "The Diagnosis and Management of Nonalcoholic Fatty Liver Disease: Practice Guidance from the American Association for the Study of Liver Diseases." Hepatology 67 (1): 328-57. https://doi.org/10.1002/hep.29367.

Chung, Goh Eun, Jeong Yoon Yim, Donghee Kim, Min-Sun Kwak, Jong In Yang, Su Jin Chung, Sun Young Yang, and Joo Sung Kim. 2017. "Associations between Hemoglobin Concentrations and the Development of Incidental Metabolic Syndrome or Nonalcoholic Fatty Liver Disease." Digestive and Liver Disease 49 (1): 57-62. https://doi.org/10.1016/j.dld.2016.10.004.

Diehl, Anna M., and Christopher Day. 2017. "Cause, Pathogenesis, and Treatment of Nonalcoholic Steatohepatitis." New England Journal of Medicine 377 (21): 2063-72. https://doi.org/10.1056/nejmra1503519.

Docherty, Matt, Stephane A Regnier, Gorana Capkun, Maria-Magdalena Balp, Qin Ye, Nico Janssens, Andreas Tietz, et al. 2021. "Development of a Novel Machine Learning Model to Predict Presence of Nonalcoholic Steatohepatitis." Journal of the American Medical Informatics Association 28 (6): 1235-41. https://doi.org/10.1093/jamia/ocab003.

Ekstedt, Mattias, Hannes Hagstrom, Patrik Nasr, Mats Fredrikson, Per Stål, Stergios Kechagias, and Rolf Hultcrantz. 2015. "Fibrosis Stage Is the Strongest Predictor for Disease-Specific Mortality in NAFLD after up to 33 Years of Follow-Up." Hepatology 61 (5): 1547-54. https://doi.org/10.1002/hep.27368.

Fialoke, Suruchi, Anders Malarstig, Melissa R. Miller, and Alexandra Dumitriu. 2018. "Application of Machine Learning Methods to Predict Non-Alcoholic Steatohepatitis (NASH) in Non-Alcoholic Fatty Liver (NAFL) Patients." AMIA . . . Annual Symposium Proceedings. AMIA Symposium. Vol. 2018.

Freund, Y, and R E Schapire. 1999. "A Short Introduction to Boosting." Journal of Japanese Society for Artificial Intelligence 14 (5): 771-80.

Giorgio, Valentina, Antonella Mosca, Arianna Alterio, Anna Alisi, Antonio Grieco, Valerio Nobili, and Luca Miele. 2017. "Elevated Hemoglobin Level Is Associated With Advanced Fibrosis in Pediatric Nonalcoholic Fatty Liver Disease." *Journal of Pediatric Gastroenterology & Nutrition* 65 (2): 150-55. https://doi.org/10.1097/MPG.0000000000001614.

Gordon, Stuart C., Jeremy Fraysse, Suying Li, A. Burak Ozbay, and Robert J. Wong. 2020. "Disease Severity Is Associated with Higher Healthcare Utilization in Nonalcoholic Steatohepatitis Medicare Patients." *American Journal of Gastroenterology* 115 (4): 562-74. https://doi.org/10.14309/ajg.0000000000000484.

Gotlieb, Neta, Naama Schwartz, Shira Zelber-Sagi, Gabriel Chodick, Varda Shalev, and Oren Shibolet. 2020. "Longitudinal Decrease in Platelet Counts as a Surrogate Marker of Liver Fibrosis." *World Journal of Gastroenterology* 26 (38): 5849-62. https://doi.org/10.3748/wjg.v26.i38.5849.

Kwo, Paul Y, Stanley M Cohen, and Joseph K Lim. 2017. "ACG Clinical Guideline: Evaluation of Abnormal Liver Chemistries." *American Journal of Gastroenterology* 112 (1): 18-35. https://doi.org/10.1038/ajg.2016.517.

Le, Michael H., Pardha Devaki, Nghiem B. Ha, Dae Won Jun, Helen S. Te, Ramsey C. Cheung, and Mindie H. Nguyen. 2017. "Prevalence of Non-Alcoholic Fatty Liver Disease and Risk Factors for Advanced Fibrosis and Mortality in the United States." *PLOS ONE* 12 (3). https://doi.org/10.1371/journal.pone.0173499.

Levitt, David G, and Michael D Levitt. 2016. "Human Serum Albumin Homeostasis: A New Look at the Roles of Synthesis, Catabolism, Renal and Gastrointestinal Excretion, and the Clinical Value of Serum Albumin Measurements." *International Journal of General Medicin*, no. 9: 229-55. https://doi.org/10.2147/IJGM.S102819.

Loomba, Rohit, Maria Abraham, Aynur Unalp, Laura Wilson, Joel Lavine, Ed Doo, and Nathan M. Bass. 2012. "Association between Diabetes, Family History of Diabetes, and Risk of Nonalcoholic Steatohepatitis and Fibrosis." *Hepatology* 56 (3): 943-51. https://doi.org/10.1002/hep.25772.

Munteanu, M., Dina Tiniakos, Q. Anstee, Frederic Charlotte, Giulio Marchesini, Elisabetta Bugianesi, Michael Trauner, et al. 2016. "Diagnostic Performance of FibroTest, SteatoTest and ActiTest in Patients with NAFLD Using the SAF Score as Histological Reference." *Alimentary Pharmacology and Therapeutics* 44 (8): 877-89. https://doi.org/10.1111/apt.13770.

Okanoue, Takeshi, Toshihide Shima, Yasuhide Mitsumoto, Atsushi Umemura, Kanji Yamaguchi, Yoshito Itoh, Masato Yoneda, et al. 2021a. "Artificial Intelligence/Neural Network System for the Screening of Nonalcoholic Fatty Liver Disease and Nonalcoholic Steatohepatitis." *Hepatology Research* 51 (5): 554-69. https://doi.org/10.1111/hepr.13628.

Okanoue, Takeshi, Toshihide Shima, Yasuhide Mitsumoto, Atsushi Umemura, Kanji Yamaguchi, Yoshito Itoh, Masato Yoneda, et al. 2021b. "Novel Artificial Intelligent/Neural Network System for Staging of Nonalcoholic Steatohepatitis." *Hepatology Research* 51 (10): 1044-57. https://doi.org/10.1111/hepr.13681.

Popa, Stefan L., Abdulrahman Ismaiel, Pop Cristina, Mogosan Cristina, Giuseppe Chiarioni, Liliana David, and Dan L. Dumitrascu. 2021. "Non-Alcoholic Fatty Liver Disease: Implementing Complete Automated Diagnosis and Staging. A Systematic Review." *Diagnostics* 11 (6): 1078. https://doi.org/10.3390/diagnostics11061078.

Portillo-Sanchez, Paola, Fernando Bril, Maryann Maximos, Romina Lomonaco, Diane Biernacki, Beverly Orsak, Sreevidya Subbarayan, Amy Webb, Joan Hecht, and Kenneth Cusi. 2015. "High Prevalence of Nonalcoholic Fatty Liver Disease in Patients With Type 2 Diabetes Mellitus and Normal Plasma Aminotransferase Levels." *The Journal of Clinical Endocrinology & Metabolism* 100 (6): 2231-38. https://doi.org/10.1210/jc.2015-1966.

Poynard, Thierry, Valerie Paradis, Jimmy Mullaert, Olivier Deckmyn, Nathalie Gault, Estelle Marcault, Pauline Manchon, et al. 2021. "Prospective External Validation of a New Non-Invasive Test for the Diagnosis of Non-Alcoholic Steatohepatitis in Patients with Type 2 Diabetes." *Alimentary Pharmacology and Therapeutics* 54 (7): 952-66. https://doi.org/10.1111/apt.16543.

Ratziu, Vlad, Julien Massard, Frederic Charlotte, Djamila Messous, Francoise Imbert-Bismut, Luninita Bonyhay, Mohamed Tahiri, et al. 2006. "Diagnostic Value of Biochemical Markers (Fibro Test-FibroSURE) for the Prediction of Liver Fibrosis in Patients with Non-Alcoholic Fatty Liver Disease." *BMC Gastroenterology* 6: 1-13. https://doi.org/10.1186/1471-230X-6-6.

Rockey, Don C., Stephen H. Caldwell, Zachary D. Goodman, Rendon C. Nelson, and Alastair D. Smith. 2009. "Liver Biopsy." *Hepatology* 49 (3): 1017-44. https://doi.org/10.1002/hep.22742.

Sirota, Jeffrey C., Kim McFann, Giovanni Targher, Michel Chonchol, and Diana I. Jalal. 2012. "Association between Nonalcoholic Liver Disease and Chronic Kidney Disease: An Ultrasound Analysis from NHANES 1988– 1994." *American Journal of Nephrology* 36 (5): 466-71. https://doi.org/10.1159/000343885.

Targher, Giovanni, Lorenzo Bertolini, Stefano Rodella, Giuseppe Lippi, Giacomo Zoppini, and Michel Chonchol. 2010. "Relationship between Kidney Function and Liver Histology in Subjects with Nonalcoholic Steatohepatitis." *Clinical Journal of the American Society of Nephrology* 5 (12): 2166-71. https://doi.org/10.2215/CJN.05050610.

Vali, Yasaman, Jenny Lee, Jerome Boursier, Rene Spijker, Joanne Verheij, M. Julia Brosnan, Quentin M. Anstee, Patrick M. Bossuyt, and Mohammad Hadi Zafarmand. 2021. "Fibrotest for Evaluating Fibrosis in Non-Alcoholic Fatty Liver Disease Patients: A Systematic Review and Meta-Analysis." *Journal of Clinical Medicine* 10 (11). https://doi.org/10.3390/jcm10112415.

Vernon, G., A. Baranova, and Z. M. Younossi. 2011. "Systematic Review: The Epidemiology and Natural History of Non-Alcoholic Fatty Liver Disease and Non-Alcoholic Steatohepatitis in Adults." *Alimentary Pharmacology & Therapeutics* 34 (3): 274-85. https://doi.org/10.1111/j.1365-2036.2011.04724.x.

Wessels, David Hermanus, and Zeil Rosenberg. 2021. "Awareness of Non-Alcoholic Steatohepatitis and Treatment Guidelines: What Are Physicians Telling Us?" *World Journal of Hepatology* 13 (2): 233-41. https://doi.org/10.4254/wjh.v13.i2.233.

Wong, Robert J., Maria Aguilar, Ramsey Cheung, Ryan B. Perumpail, Stephen A. Harrison, Zobair M. Younossi, and Aijaz Ahmed. 2015. "Nonalcoholic Steatohepatitis Is the Second Leading Etiology of Liver Disease among Adults Awaiting Liver Transplantation in the United States." *Gastroenterology* 148 (3): 547-55. https://doi.org/10.1053/j.gastro.2014.11.039.

Yang, Wen, Haiyan Huang, Yuzhu Wang, Xiaohong Yu, and Zhijian Yang. 2014. "High Red Blood Cell Distribution Width Is Closely Associated with Nonalcoholic Fatty Liver Disease." *European Journal of Gastroenterology & Hepatology* 26 (2): 174-78. https://doi.org/10.1097/MEG.0b013e328365c403.

Yoneda, Masato, Hideki Fujii, Yoshio Sumida, Hideyuki Hyogo, Yoshito Itoh, Masafumi Ono, Yuichiro Eguchi, et al. 2011. "Platelet Count for Predicting Fibrosis in Non-alcoholic Fatty Liver Disease." *Journal of Gastroenterology* 46 (11): 1300-1306. https://doi.org/10.1007/s00535-011-0436-4.

Younossi, Zobair M., Pegah Golabi, Leyla de Avila, James Minhui Paik, Manirath Srishord, Natsu Fukui, Ying Qiu, Leah Burns, Arian Afendy, and Fatema Nader. 2019. "The Global Epidemiology of NAFLD and NASH in Patients with Type 2 Diabetes: A Systematic Review and Meta-Analysis." *Journal of Hepatology* 71 (4): 793-801. https://doi.org/10.1016/j.jhep.2019.06.021.

Younossi, Zobair M., Aaron B. Koenig, Dinan Abdelatif, Yousef Fazel, Linda Henry, and Mark Wymer. 2016. "Global Epidemiology of Nonalcoholic Fatty Liver Disease-Meta-Analytic Assessment of Prevalence, Incidence, and Outcomes." *Hepatology* 64 (1): 73-84. https://doi.org/10.1002/hep.28431.

Younossi, Zobair M., Maria Stepanova, Nila Rafiq, Hala Makhlouf, Zahra Younoszai, Ritambhara Agrawal, and Zachary Goodman. 2011. "Pathologic Criteria for Non-alcoholic Steatohepatitis: Interprotocol Agreement and Ability to Predict Liver-Related Mortality." *Hepatology* 53 (6): 1874-82. https://doi.org/10.1002/hep.24268.

Younossi, Zobair M., Radhika Tampi, Massoom Priyadarshini, Fatema Nader, Issah M. Younossi, and Andrei Racila. 2019. "Burden of Illness and Economic Model for Patients With Nonalcoholic Steatohepatitis in the United States." *Hepatology* 69 (2): 564-72. https://doi.org/10.1002/hep.30254.

Younossi, Zobair M, Maria Stepanova, Youssef Younossi, Pegah Golabi, Alita Mishra, Nila Rafiq, and Linda Henry. 2020. "Epidemiology of Chronic Liver Diseases in the USA in the Past Three Decades." *Gut* 69 (3): 564-68. https://doi.org/10.1136/gutjnl-2019-318813.

Additional Considerations

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine-readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine-readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method comprising:

obtaining datasets for subjects, wherein each of the datasets comprises subject features, wherein the subject features comprise an index and historical laboratory test results corresponding to test codes;

filtering the datasets based on a denoise-balance scheme to obtain a plurality of subsets of filtered datasets, wherein the denoise-balance scheme comprises at least one of an index filter, a test code filter, a feature filter, and a balance filter, and wherein the filtered datasets comprise filtered features;

training a machine learning model using a first subset of the plurality of subsets, wherein the first subset of the filtered datasets comprises: (i) a set of outcome predictor datasets including historical laboratory test results for subjects that tested abnormal for a clinical diagnostic test, and (ii) a set of control datasets including historical laboratory test results for subjects that tested normal for the clinical diagnostic test;

validating the machine learning model using a second subset of the plurality of subsets;

adjusting the machine learning model by repeating the training and the validating until a predetermined condition is satisfied;

in response to the adjusting, obtaining a set of model parameters; and providing the trained machine learning model having the set of model parameters.

2. The computer-implemented method of claim 1, wherein the filtering the datasets comprises:

denoising the subject features based on the index filter, wherein the denoising comprises removing a first set of the datasets from the datasets;

denoising the subject features based on the test code filter, wherein the denoising comprises removing a second set of the datasets from the datasets;

obtaining at least two subsets of the datasets based on a historical laboratory test result corresponding to a predetermined test code, wherein the historical laboratory test is in the subject features;

calculating a feature number for each subject feature in each subset based on the feature filter;

sorting a total feature number, wherein the total feature number is a sum of at least two of the feature numbers for the at least two subsets;

denoising the subject features based on the feature filter, wherein the denoising comprises removing a third set of the datasets from the datasets; and balancing the feature numbers based on the balance filter, wherein a ratio of the at least two feature numbers is in a predetermined range, wherein the balancing comprises removing a fourth set of the datasets from the datasets.

3. The computer-implemented method of claim 2, wherein the obtaining the at least two subsets of the datasets comprises removing datasets from at least one of the at least two subsets, and wherein the calculating the feature number comprises removing datasets from the at least two subsets to maintain a predetermined ratio scope between the at least two subsets.

4. The computer-implemented method of claim 2, wherein the predetermined test code is (i) a Non-Alcoholic Steatohepatitis (NASH) fibrosis score test code, (ii) an albumin/creatinine ratio (ACR) test code, or (iii) an estimated glomerular filtration rate (eGFR) test code.

5. The computer-implemented method of claim 1, wherein the training the machine learning model further comprises:

training an ensemble of classifiers implemented with a boosting algorithm on the first subset by applying base machine learning algorithms on different distributions of the first subset, wherein the training causes the ensemble of classifiers to learn a function that maps a training input space derived from the first subset to a target output space such that the function is an accurate predictor for the target output space, wherein the target output space is a result of the clinical diagnostic test, and wherein the function is learned by finding the set of model parameters that minimize a cost function that measures a difference between ground truth values for the subjects that tested abnormal or normal for the clinical diagnostic test and predicted results of the clinical diagnostic test; and combining the ensemble of classifiers into the trained machine learning model having the set of model parameters for predicting the result for the clinical diagnostic test.

6. The computer-implemented method of claim 1, further comprising:

obtaining a dataset for a subject, wherein the dataset comprises an index and historical laboratory test results corresponding to test codes;

inputting the dataset into the trained machine learning model;

predicting, using the trained machine learning model, a result for a clinical diagnostic test; and outputting, using the trained machine learning model, a classification of the clinical diagnostic test based on the result for the clinical diagnostic test.

7. A computer-program product tangibly embodied in a non-transitory machine-readable medium, including instructions configured to cause one or more data processors to perform:

obtaining datasets for subjects, wherein each of the datasets comprises subject features, wherein the subject features comprise an index and historical laboratory test results corresponding to test codes;

filtering the datasets based on a denoise-balance scheme to obtain a plurality of subsets of filtered datasets, wherein the denoise-balance scheme comprises at least one of an index filter, a test code filter, a feature filter, and a balance filter, and wherein the filtered datasets comprise filtered features;

training a machine learning model using a first subset of the plurality of subsets, wherein the first subset of the filtered datasets comprises: (i) a set of outcome predictor datasets including historical laboratory test results for subjects that tested abnormal for a clinical diagnostic test, and (ii) a set of control datasets including historical laboratory test results for subjects that tested normal for the clinical diagnostic test;

validating the machine learning model using a second subset of the plurality of subsets;

adjusting the machine learning model by repeating the training and the validating until a predetermined condition is satisfied;

in response to the adjusting, obtaining a set of model parameters; and providing the trained machine learning model having the set of model parameters.

8. The computer-program product of claim 7, wherein the filtering the datasets comprises:

denoising the subject features based on the index filter, wherein the denoising comprises removing a first set of the datasets from the datasets;

denoising the subject features based on the test code filter, wherein the denoising comprises removing a second set of the datasets from the datasets;

obtaining at least two subsets of the datasets based on a historical laboratory test result corresponding to a predetermined test code, wherein the historical laboratory test is in the subject features;

calculating a feature number for each subject feature in each subset based on the feature filter;

sorting a total feature number, wherein the total feature number is a sum of at least two of the feature numbers for the at least two subsets;

denoising the subject features based on the feature filter, wherein the denoising comprises removing a third set of the datasets from the datasets; and balancing the feature numbers based on the balance filter, wherein a ratio of the at least two feature numbers is in a predetermined range, wherein the balancing comprises removing a fourth set of the datasets from the datasets.

9. The computer-program product of claim 8, wherein the obtaining the at least two subsets of the datasets comprises removing datasets from at least one of the at least two subsets, and wherein the calculating the feature number comprises removing datasets from the at least two subsets to maintain a predetermined ratio scope between the at least two subsets.

10. The computer-program product of claim 8, wherein the predetermined test code is (i) a Non-Alcoholic Steatohepatitis (NASH) fibrosis score test code, (ii) an albumin/creatinine ratio (ACR) test code, or (iii) an estimated glomerular filtration rate (eGFR) test code.

11. The computer-program product of claim 7, wherein the training the machine learning model further comprises:

training an ensemble of classifiers implemented with a boosting algorithm on the first subset by applying base machine learning algorithms on different distributions of the first subset, wherein the training causes the ensemble of classifiers to learn a function that maps a training input space derived from the first subset to a target output space such that the function is an accurate predictor for the target output space, wherein the target output space is a result of the clinical diagnostic test, and wherein the function is learned by finding the set of model parameters that minimize a cost function that measures a difference between ground truth values for the subjects that tested abnormal or normal for the clinical diagnostic test and predicted results of the clinical diagnostic test; and having the set of model parameters for predicting the result for the clinical diagnostic test.

12. The computer-program product of claim 7, wherein the one or more data processors are caused to further perform:

obtaining a dataset for a subject, wherein the dataset comprises an index and historical laboratory test results corresponding to test codes;

inputting the dataset into the trained machine learning model;

predicting, using the trained machine learning model, a result for a clinical diagnostic test; and outputting, using the trained machine learning model, a classification of the clinical diagnostic test based on the result for the clinical diagnostic test.

13. A system comprising:

one or more data processors; and a non-transitory computer readable medium storing instructions which, when executed on the one or more data processors, cause the one or more data processors to perform:

obtaining datasets for subjects, wherein each of the datasets comprises subject features, wherein the subject features comprise an index and historical laboratory test results corresponding to test codes;

filtering the datasets based on a denoise-balance scheme to obtain a plurality of subsets of filtered datasets, wherein the denoise-balance scheme comprises at least one of an index filter, a test code filter, a feature filter, and a balance filter, and wherein the filtered datasets comprise filtered features;

training a machine learning model using a first subset of the plurality of subsets, wherein the first subset of the filtered datasets comprises: (i) a set of outcome predictor datasets including historical laboratory test results for subjects that tested abnormal for a clinical diagnostic test, and (ii) a set of control datasets including historical laboratory test results for subjects that tested normal for the clinical diagnostic test;

validating the machine learning model using a second subset of the plurality of subsets;

adjusting the machine learning model by repeating the training and the validating until a predetermined condition is satisfied;

in response to the adjusting, obtaining a set of model parameters; and providing the trained machine learning model having the set of model parameters.

14. The system of claim 13, wherein the filtering the datasets comprises:

denoising the subject features based on the index filter, wherein the denoising comprises removing a first set of the datasets from the datasets;

denoising the subject features based on the test code filter, wherein the denoising comprises removing a second set of the datasets from the datasets;

obtaining at least two subsets of the datasets based on a historical laboratory test result corresponding to a predetermined test code, wherein the historical laboratory test is in the subject features;

calculating a feature number for each subject feature in each subset based on the feature filter;

sorting a total feature number, wherein the total feature number is a sum of at least two of the feature numbers for the at least two subsets;

denoising the subject features based on the feature filter, wherein the denoising comprises removing a third set of the datasets from the datasets; and balancing the feature numbers based on the balance filter, wherein a ratio of the at least two feature numbers is in a predetermined range, wherein the balancing comprises removing a fourth set of the datasets from the datasets.

15. The system of claim 14, wherein the obtaining the at least two subsets of the datasets comprises removing datasets from at least one of the at least two subsets, wherein the calculating the feature number comprises removing datasets from the at least two subsets to maintain a predetermined ratio scope between the at least two subsets, and wherein the predetermined test code is (i) a Non-Alcoholic Steatohepatitis (NASH) fibrosis score test code, (ii) an albumin/creatinine ratio (ACR) test code, or (iii) an estimated glomerular filtration rate (eGFR) test code.

16. The system of claim 13, wherein the training the machine learning model further comprises:

training an ensemble of classifiers implemented with a boosting algorithm on the first subset by applying base machine learning algorithms on different distributions of the first subset, wherein the training causes the ensemble of classifiers to learn a function that maps a training input space derived from the first subset to a target output space such that the function is an accurate predictor for the target output space, wherein the target output space is a result of the clinical diagnostic test, and wherein the function is learned by finding the set of model parameters that minimize a cost function that measures a difference between ground truth values for the subjects that tested abnormal or normal for the clinical diagnostic test and predicted results of the clinical diagnostic test; and combining the ensemble of classifiers into the trained machine learning model having the set of model parameters for predicting the result for the clinical diagnostic test.

17. The system of claim 13, wherein the one or more data processors are caused to further perform:

obtaining a dataset for a subject, wherein the dataset comprises an index and historical laboratory test results corresponding to test codes;

inputting the dataset into the trained machine learning model;

predicting, using the trained machine learning model, a result for a clinical diagnostic test; and outputting, using the trained machine learning model, a classification of the clinical diagnostic test based on the result for the clinical diagnostic test.

\* \* \* \* \*